(12) United States Patent
Renzi et al.

(10) Patent No.: US 11,386,979 B2
(45) Date of Patent: Jul. 12, 2022

(54) METHOD AND SYSTEM FOR STORING AND ACCESSING BIOINFORMATICS DATA

(71) Applicant: GenomSys SA, Lausanne (CH)

(72) Inventors: Daniele Renzi, Lausanne (CH); Giorgio Zoia, Lausanne (CH)

(73) Assignee: GENOMSYS SA, Lausanne (CH)

( * ) Notice: Subject to any disclaimer, the term of this patent is extended or adjusted under 35 U.S.C. 154(b) by 426 days.

(21) Appl. No.: 16/341,373

(22) PCT Filed: Oct. 11, 2016

(86) PCT No.: PCT/EP2016/074301
§ 371 (c)(1),
(2) Date: Apr. 11, 2019

(87) PCT Pub. No.: WO2018/068828
PCT Pub. Date: Apr. 19, 2018

(65) Prior Publication Data
US 2020/0058378 A1    Feb. 20, 2020

(51) Int. Cl.
| | | |
|---|---|---|
| G01N 33/48 | (2006.01) | |
| G01N 33/50 | (2006.01) | |
| G16B 50/30 | (2019.01) | |
| G16B 30/10 | (2019.01) | |
| G16B 40/10 | (2019.01) | |
| G16B 50/20 | (2019.01) | |
| G06F 17/16 | (2006.01) | |
| G06F 17/18 | (2006.01) | |
| C12Q 1/6869 | (2018.01) | |

(52) U.S. Cl.
CPC ............. *G16B 50/30* (2019.02); *G06F 17/16* (2013.01); *G06F 17/18* (2013.01); *G16B 30/10* (2019.02); *G16B 40/10* (2019.02); *G16B 50/20* (2019.02); *C12Q 1/6869* (2013.01)

(58) Field of Classification Search
CPC ........ G16B 50/30; G16B 30/10; G16B 40/10; G16B 50/20; G06F 17/16; G06F 17/18; C12Q 1/6869
See application file for complete search history.

(56) References Cited

U.S. PATENT DOCUMENTS

| | | | |
|---|---|---|---|
| 2008/0077607 A1* | 3/2008 | Gatawood | ............... G06F 16/22 |
| 2012/0089339 A1* | 4/2012 | Ganeshalingam | ...... G06F 16/22 702/19 |

(Continued)

FOREIGN PATENT DOCUMENTS

| | | |
|---|---|---|
| JP | 2003-188735 | 7/2003 |
| JP | 2004-240975 | 8/2004 |

(Continued)

OTHER PUBLICATIONS

Craig et al. Ordering of cosmid clones covering the Herpes simplex virus type I (HSV-I) genome: a test case for fingerprinting by hybridisation. Nucleic Acids Research, vol. 18, pp. 2653-2660. (Year: 1990).*

(Continued)

*Primary Examiner* — Russell S Negin
(74) *Attorney, Agent, or Firm* — Dickinson Wright PLLC

(57) ABSTRACT

Method and system for storing and accessing genomic data. Genomic sequencing data are partitioned into access units of different types based on the predictability of the contained data. Access units are classified in different types and the structuring enables selective access and selective processing of genomic data.

22 Claims, 25 Drawing Sheets

EXAMPLE
Constant reads length = 100

Pair 1 = Read 1 + Read 2
Pair 2 = Read 3 + Read 4
Pair 3 = Read 5 + Read 6

Read 1    Read 3    Read 2              Read 6    Read 5
Reference sequence 1
                        Read 4
Reference sequence 4
p0 = 0    p1 = 10000    p3 = 10180    p2 = 10320    p4 = 10450    p6 = 10620    p5 = 10850

Pairing distances | 220 | 0xffffff | 4 | 170 | -330 | reserved value (flag)

reference sequence id if different from current reference p2 − p1 − 100 = 220
p4 − p3 − 100 = 170
p6 − p5 − 100 = −330

When a read is mapped on a difference reference than its mate (read 4), additional descriptors are added to the pairing distance. One is a signaling flag, the second is a reference identifier and then the pairing distance.

(56) References Cited

U.S. PATENT DOCUMENTS

2014/0289536 A1\* 9/2014 MacCarthy ............. G06F 21/62
713/189
2015/0227686 A1 8/2015 Sheinin et al.

FOREIGN PATENT DOCUMENTS

JP 2007-193708 8/2007
WO 2018068828 4/2018

OTHER PUBLICATIONS

Patent Cooperation Treaty—PCT—Third Part Observation, filed on related international application PCT/EP2016/074301, Date of Submission Feb. 8, 2019 (dated Aug. 2, 2019).

CRAM format specification (version 3.0), dated Jun. 1, 2015 (Jan. 6, 2015), https://githum.com/samtools/hts-specs, 26 pages.
Samtools—Utilities for the Sequence Alignment/Map (SAM) format, dated Dec. 15, 2015 (Dec. 15, 2015), Manual page from samtools, http://www.htslib.org/doc/samtools-1.3html, 22 pages.
Notice of Reasons for Refusal dated Dec. 23, 2020 (Japanese Office Action) issued on related Japanese patent application JP-2019-520450 by the Japanese Patent Office.
Anonymous, Sequence Alignment/Map Format Specification—The SAM/BAM Format Specification Working Group, Retrieved from the Internet: URL:http0/03A//samtools.github.io/hts-specs/SAMv1. pdf, Jan. 30, 2019, pp. 1-21.
Anonymous, CRAM format specification (Version 3.0), Retrieved from the Internet: URL:https://samtools.github.io/hts-specs/CRAMv3. pdf, Apr. 5, 2019, pp. 1-37.

\* cited by examiner

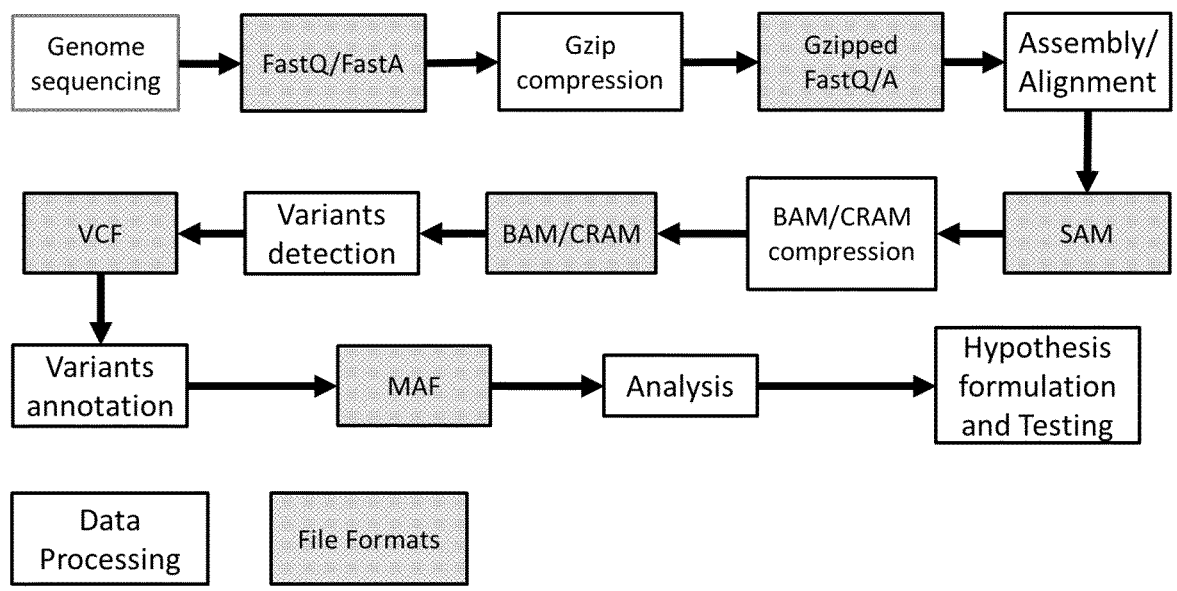
Figure 1 - Typical genome processing pipeline and file formats.
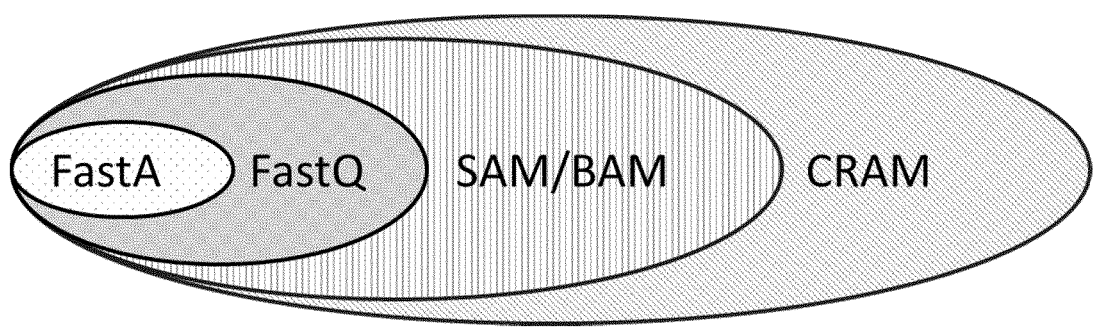
Figure 2 - Genomic file formats and their relation.
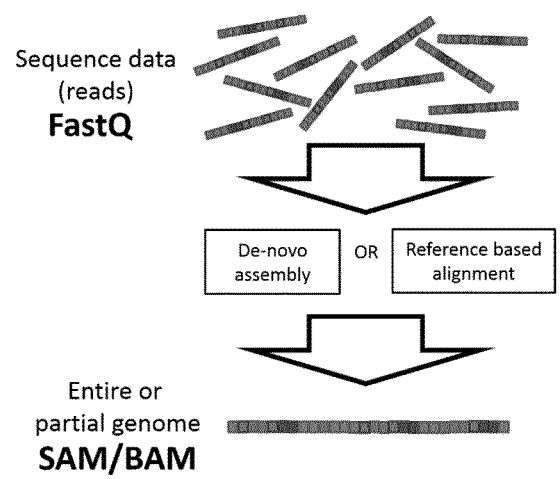
Figure 3 - Genome sequence reads alignment.

| Read 1 | Read 3 | Read 2 | Read 4 | Read 6 | Read 5 |

*Reference sequence* p0 = 0   p1 = 10000   p3 = 10180   p2 = 10320   p4 = 10450   p6 = 10620   p5 = 10850 pos Layer | 10000 | 180 | 670 | p3 − p1 = 180
p5 − p3 = 670

Figure 4 - How the position of the first read of three read pairs mapped are encoded in the pos layer.

EXAMPLE
Constant reads length = 100

| Read 1 | Read 3 | Read 2 | Read 4 | Read 6 | Read 5 |

*Reference sequence* p0 = 0   p1 = 10000   p3 = 10180   p2 = 10320   p4 = 10450   p6 = 10620   p5 = 10850

Pairing distances | 220 | 170 | -330 | p2 − p1 − 100 = 220
p4 − p3 − 100 = 170
p6 − p5 − 100 = −330

Figure 5 - Calculation of pairing distance for three read pairs.

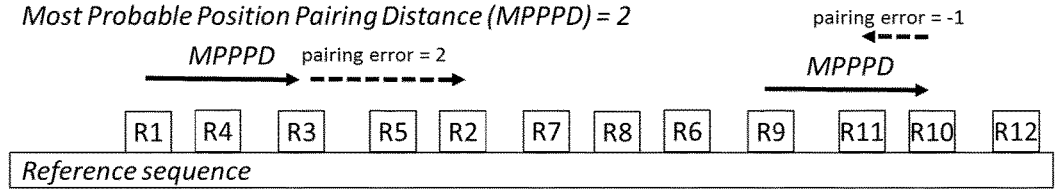
Figure 6 - Calculation of pairing errors.
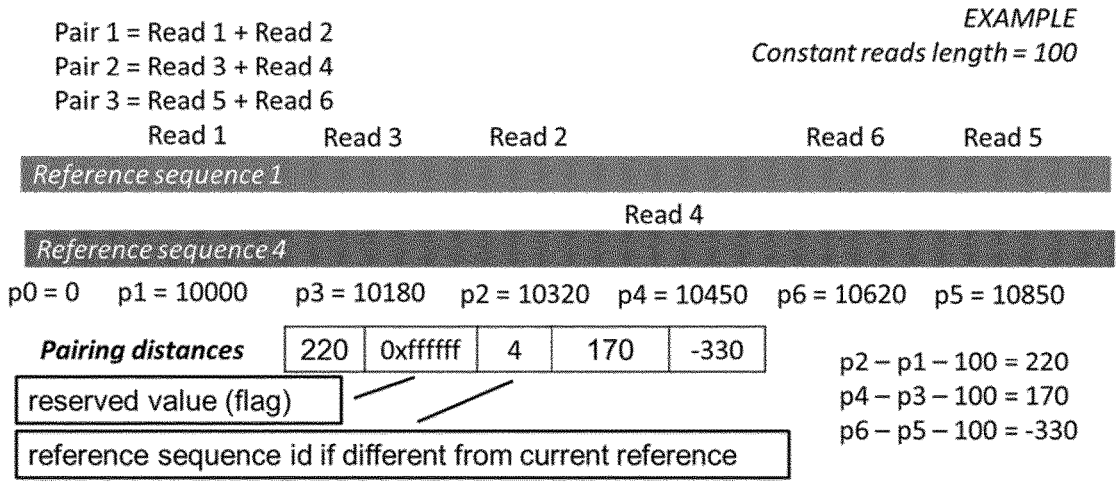
Figure 7 - When a read is mapped on a difference reference than its mate (read 4), additional descriptors are added to the pairing distance. One is a signaling flag, the second is a reference identifier and then the pairing distance.

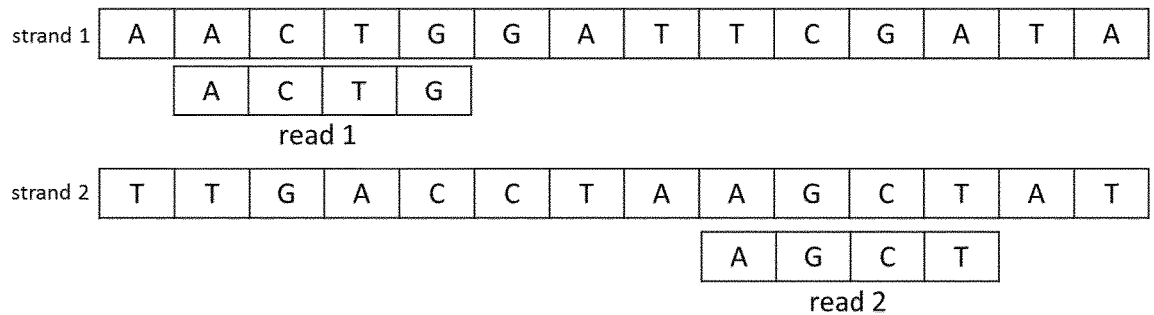
Figure 8 - In this reads pair read 1 comes from strand 1 and read 2 from strand 2.
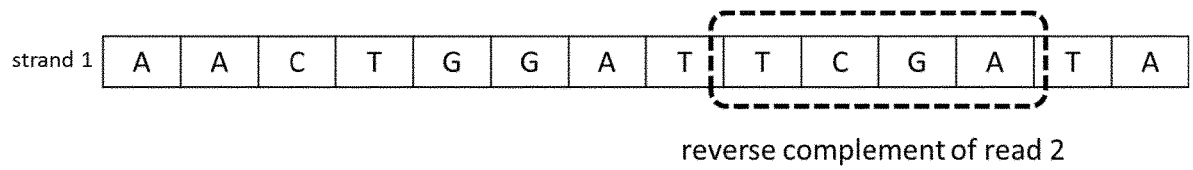
Figure 9 - The reverse complement of read 2 will be encoded if strand 1 is used as reference.
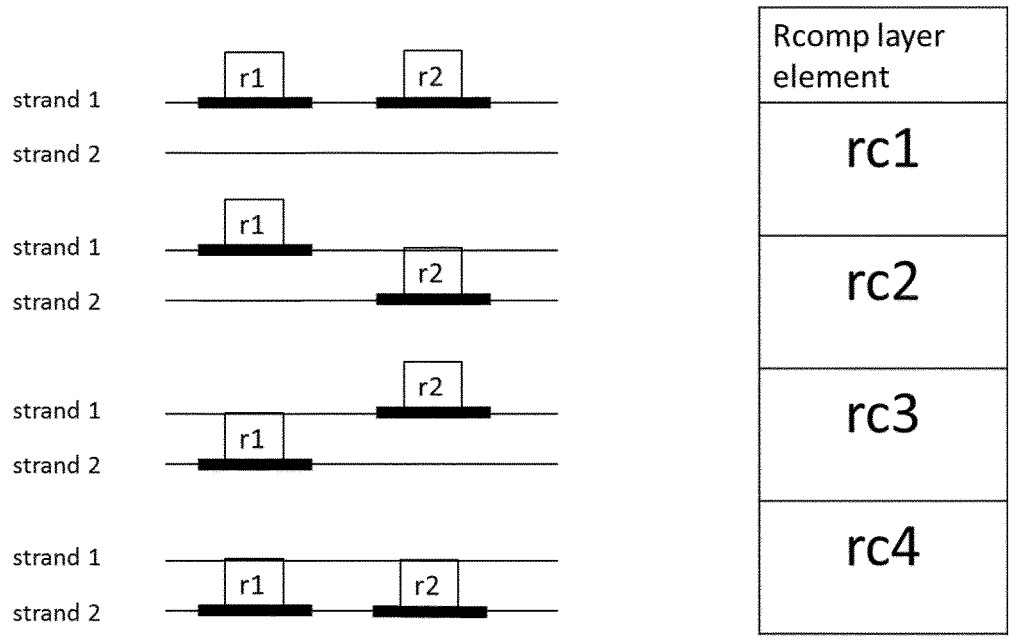
Figure 10 - The four possible combinations of reads composing a reads pair and the respective encoding in the rcomp layer.

| Ref. | A | A | C | T | G | G | A | T | T | C | G | A | T | A |

| | A | N | T | N |
| Read 1 |

| N | G | A | N |
| Read 2 | nmis layer

| 1 | 3 | 4 | 7 | S | | | | | | nmis layer (differential enc.)

| 1 | 2 | 1 | 3 | S | | | | | |

Figure 11 - Calculation of N mismatches in a nmis layer.

| Ref. | A | A | C | T | G | G | A | T | T | C | G | A | T | A |

| A | T | T | N |
| Read 1 |

| T | G | A | N |
| Read 2 |

Figure 12 - Substitutions in a mapped reads pair.

| Ref. | A | A | C | T | G | G | A | T | T | C | G | A | T | A |

| A | C | G | N |
| Read 1 |

| C | N | | T |
| Read 2 |

Snpp layer

| 2 | 3 | 5 | 6 | S | | | | | |

Snpp layer (diff. enc.)

| 2 | 1 | 2 | 1 | S | | | | | |

Figure 13 - Calculation of substitutions position either as absolute or differential values.

snpt Layer (without IUPAC codes)

A substitution type is calculated as index of a substitutions vector composed by all the possible symbols. For example:

S = [A, C, G, T, N, Z] where Z = deletion

Index direction
- ENCODING is from right to left
- DECODING from left to right

| Ref | Read | Encoded Symb. |
|-----|------|---------------|
| A | del. | idx(A,Z) = 5 |
| C | del. | idx(C,Z) = 4 |
| G | del. | idx(G,Z) = 3 |
| T | del. | idx(T,Z) = 2 |

| Ref | Read | Encoded Symb. |
|-----|------|---------------|
| N | A | idx(N,A) = 2 |
| N | C | idx(N,C) = 3 |
| N | G | idx(N,G) = 4 |
| N | T | idx(N,T) = 5 |

| Ref | Read | Encoded Symb. |
|-----|------|---------------|
| A | C | idx(A,C) = 1 |
| A | G | idx(A,G) = 2 |
| A | T | idx(A,T) = 3 |
| A | N | idx(A,N) = 4 |
| C | A | idx(C,A) = 5 |
| C | G | idx(C,G) = 1 |
| C | T | idx(C,T) = 2 |
| C | N | idx(C,N) = 3 |
| G | A | idx(G,A) = 4 |
| G | C | idx(G,C) = 5 |
| G | T | idx(G,T) = 1 |
| G | N | idx(G,N) = 2 |
| T | A | idx(T,A) = 3 |
| T | C | idx(T,C) = 4 |
| T | G | idx(T,G) = 5 |
| T | N | idx(T,N) = 1 |

Figure 14 - Calculations of symbols encoding substitutions without IUPAC codes.

| Ref. | A | A | C | T | G | G | A | T | T | C | G | A | T | A |
|------|---|---|---|---|---|---|---|---|---|---|---|---|---|---|
|      |   | A | C | G | N |   |   |   |   | C | N |   | T |   |
|      |   | Read 1 |   |   |   |   |   |   |   | Read 2 |   |   |   |   |

| Snpp layer (diff. enc.) | 2 | 1 | 2 | 1 | S | | | | | |
|---|---|---|---|---|---|---|---|---|---|---|

| Snpt layer | 1 | 4 | 4 | 5 | S | | | | | |
|---|---|---|---|---|---|---|---|---|---|---|

| Snpt layer (diff. enc.) | 1 | 3 | 0 | 1 | S | | | | | |
|---|---|---|---|---|---|---|---|---|---|---|

Figure 15 - Encoding of substitutions into the snpt layer.

snpt Layer (with IUPAC codes)

A substitution type is calculated as index in a substitutions vector composed by all the possible symbols. For example:

S = [A, C, G, T, N, Z, M, R, W, S, Y, K, V, H, D, B]

Index direction
- ENCODING is from right to left
- DECODING from left to right

| Ref | Read | Encoded Symb. |
|---|---|---|
| D | M | idx(D,M) = 8 |
| A | Y | idx(A,Y) = 10 |
| A | T | idx(A,T) = 3 |
| A | N | idx(A,N) = 4 |
| C | R | idx(C,R) = 6 |
| C | G | idx(C,G) = 1 |
| C | T | idx(C,T) = 2 |
| C | W | idx(C,W) = 7 |
| G | H | idx(G,H) = 11 |
| G | C | idx(G,C) = 15 |
| G | B | idx(G,B) = 13 |
| G | N | idx(G,N) = 2 |
| T | A | idx(T,A) = 13 |
| T | M | idx(T,M) = 4 |
| T | K | idx(T,K) = 8 |
| T | V | idx(T,V) = 9 |

| Ref | Read | Encoded Symb. |
|---|---|---|
| N | M | idx(N,M) = 2 |
| N | W | idx(N,W) = 4 |
| N | S | idx(N,S) = 5 |
| N | B | idx(N,B) = 11 |

Figure 16 - Calculations of symbols encoding substitutions with IUPAC codes.

Figure 17 – Alternative source model for substitution where only positions are encoded, but one layer per substitution type is used.

indt Layer (without IUPAC codes)

S = [A, C, G, T, N, Z]

Direction
- ENCODING is from right to left
- DECODING from left to right

| Insert | Encoded Sym. |
|---|---|
| A | 6 |
| C | 7 |
| G | 8 |
| T | 9 |
| N | 10 |

| Ref. | A | A | C | T | G | G | A | T | T | C | G | | T | C |
|---|---|---|---|---|---|---|---|---|---|---|---|---|---|---|
| | A | C | | T | G | | | | | C | N | T | T | |

Read 1        Read 2

| indp layer (diff. enc.) | 1 | 1 | 4 | 1 | S | | | | |
|---|---|---|---|---|---|---|---|---|---|

| indt layer | 5 | 2 | 4 | 9 | S | | | | |
|---|---|---|---|---|---|---|---|---|---|

| indt layer (diff. enc.) | 5 | -3 | 2 | 5 | S | | | | |
|---|---|---|---|---|---|---|---|---|---|

Figure 18 - Encoding substitutions, inserts and deletions in a reads pair of class I when IUPAC codes are not used.

indt Layer (with IUPAC codes)

S = [A, C, G, T, N, Z, M, R, W, S, Y, K, V, H, D, B]
Direction
- ENCODING is from right to left
- DECODING from left to right

| Insert | Encoded Sym. |
|---|---|
| A | 16 |
| C | 17 |
| G | 18 |
| T | 19 |
| N | 20 |

Ref. | A | A | C | T | G | G | A | T | T | C | G | | T | C |

Read 1: A | C | | T | G

Read 2: C | R | T | W

| snpp layer (diff. enc.) | 1 | 1 | 4 | 1 | 1 | S | | | |
| indt layer | 15 | 4 | 5 | 19 | 5 | S | | | |
| indt layer (diff. enc.) | 15 | -11 | 1 | 18 | -14 | S | | | |

Figure 19 - Encoding substitutions, inserts and deletions in a reads pair of class I when IUPAC codes are used.

| Unique ID | Version | Header Size | Ref count | NBlocks | Ref Ids | M.I.T. |
|---|---|---|---|---|---|---|

Figure 20 – Header of the encoded genomic information.

| Type | 1 | 2 | 3 | ... | N |
|---|---|---|---|---|---|
| Class P ptr | | | | | |
| Class N ptr | | | | | |
| Class M ptr | | | | | |
| Class I ptr | | | | | |
| Metadata | | | | | |
| Metadata | | | | | |

Access Units mapping positions

Position on the reference sequence of the first read in each AU

These pointers are used to "jump" to physical positions in the reference sequence Figure 21 – The Master Index Table contains the positions on the reference sequences of the first read in each AU.

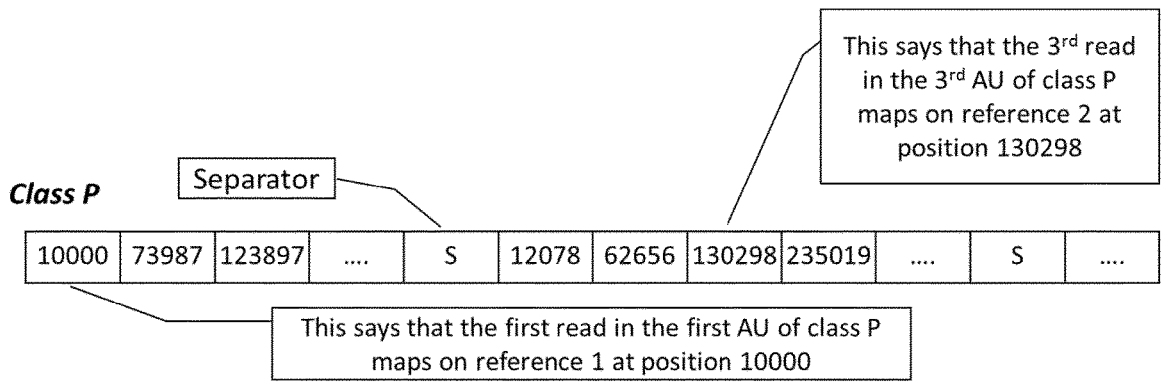

Figure 22 – Example of partial MIT showing the mapping positions of the first read in each pos AU of class P.

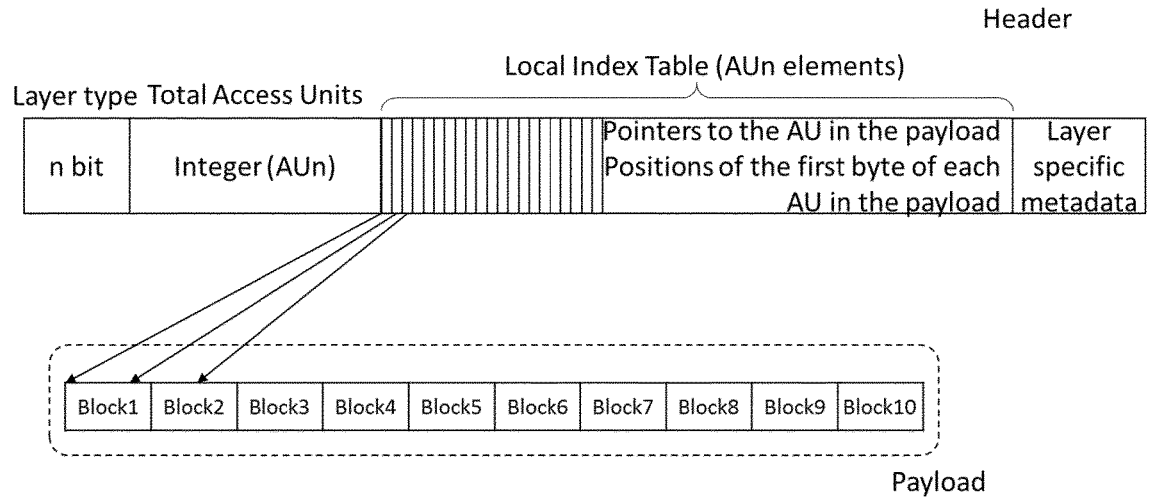
Figure 23 – The Local Index Table in the layer header is a vector of pointers to the Aus in the payload.
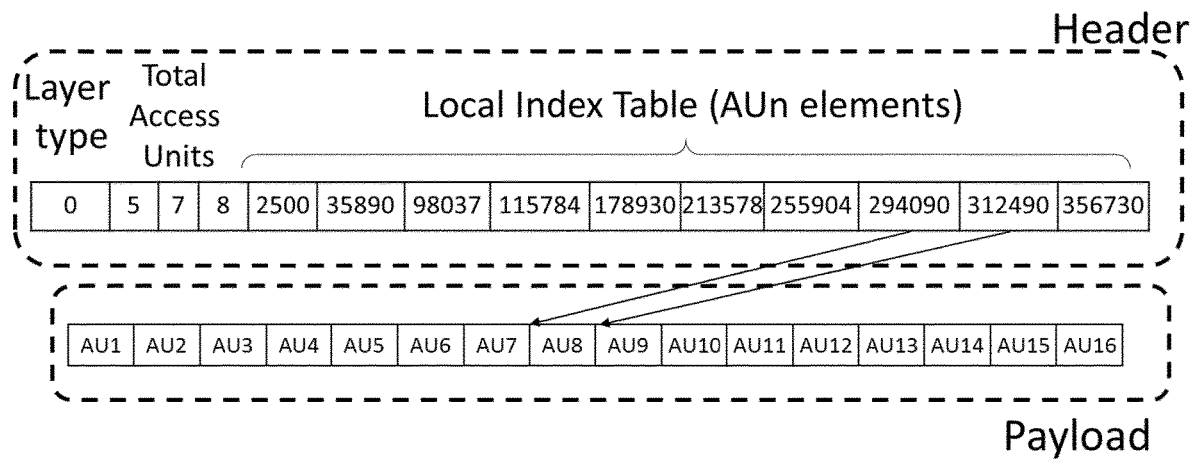
Figure 24 – Example of Local Index Table.

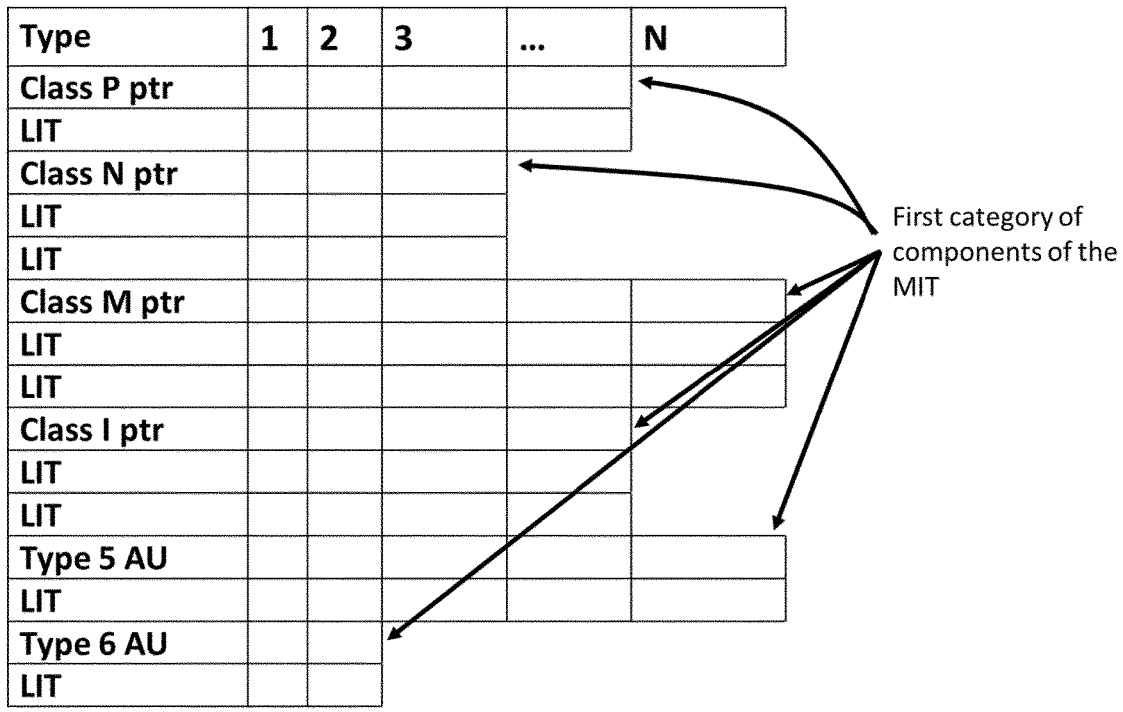
Figure 25 – Functional relation between Master Index Table and Local Index Tables.
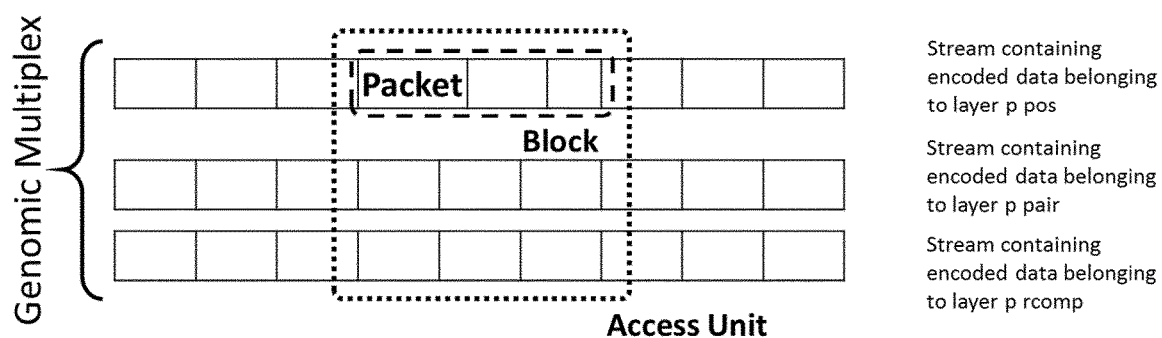
Figure 26 – Access Units are composed by blocks of data belonging to several layers and indexed using the MIT and LIT mechanisms.

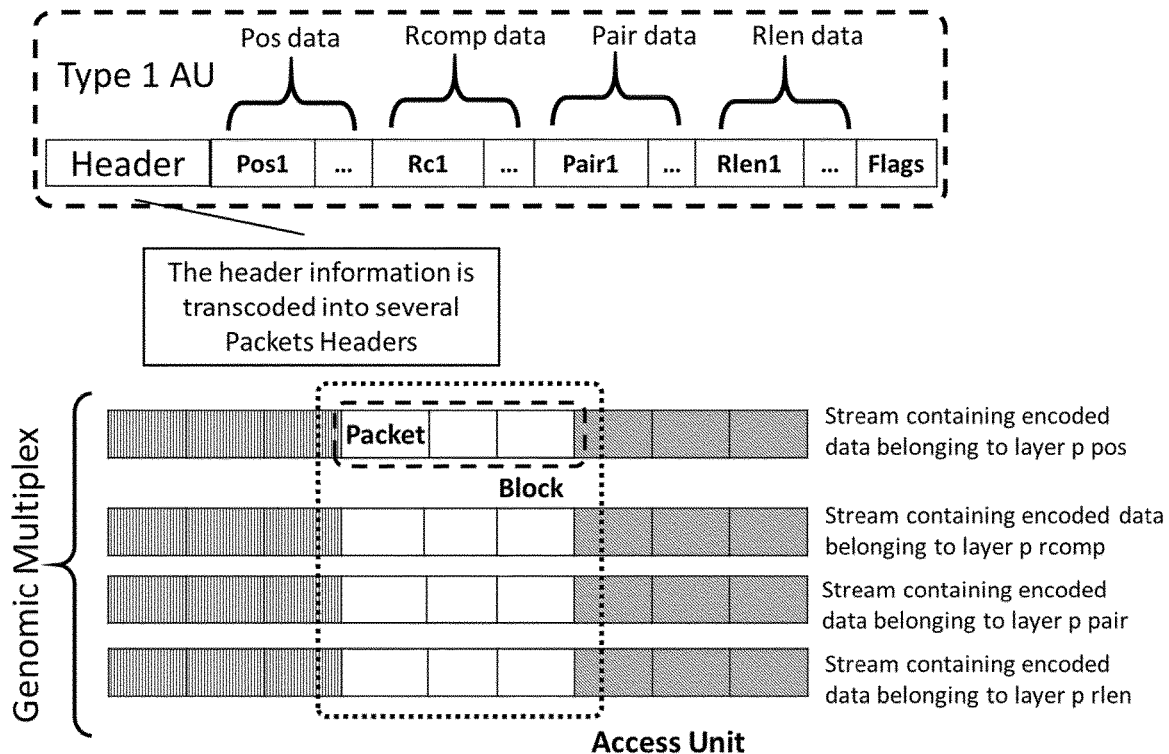
Figure 27 - An Access Unit of Type 1 is packetized and transported in a Genomic Data Multiplex.
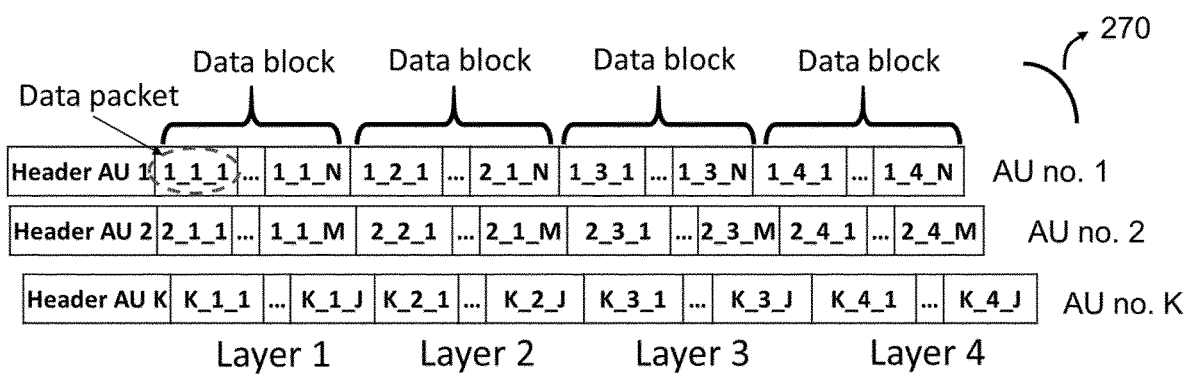
Figure 28 - Access Units are composed by a header and multiplexed blocks belonging to one or more layers of homogeneous data. Each block can be composed by one or more packets containing the actual descriptors of the genomic information.

Type 0
An Access Unit of type 0 is composed by a header and a portion of the reference sequence used to align the encoded data.
It is used to encode the reads as positions and mismatches with respect to the reference

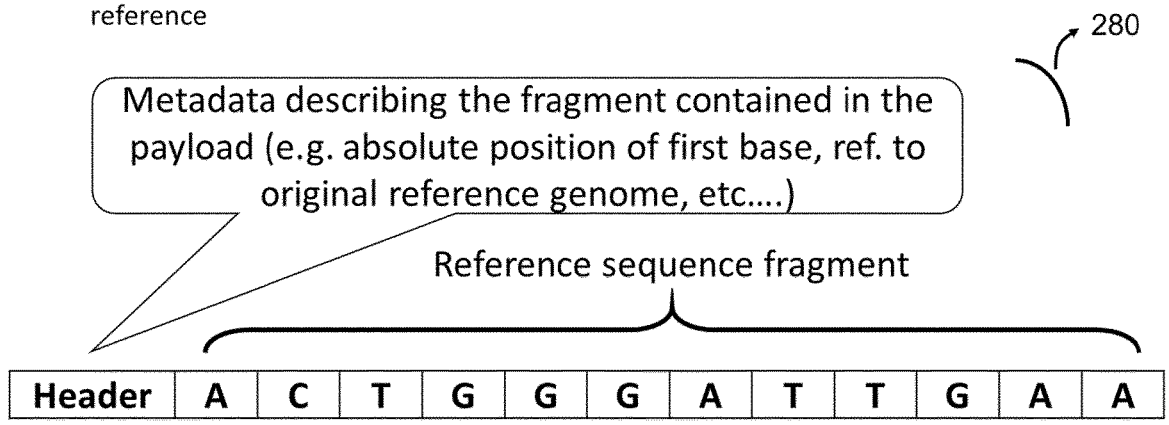

Figure 29 - Access units of type 0 do not need to refer to any information coming from other access units to be accessed or decoded and accessed.

Type 1
An Access Unit of type 1 is composed by a header and the multiplexing of data blocks of type pos, rcomp, pair (optional) and rlen (optional).
It is used to encode reads of class P

- Pos: reads position on the reference (1 per class)
- Rcomp: reverse compl. Flag (1 per class)
- Pair: pairing information (1 per class)
- Rlen: (optional) reads length in case of variable reads length
- Flags: specific characteristics of the reads

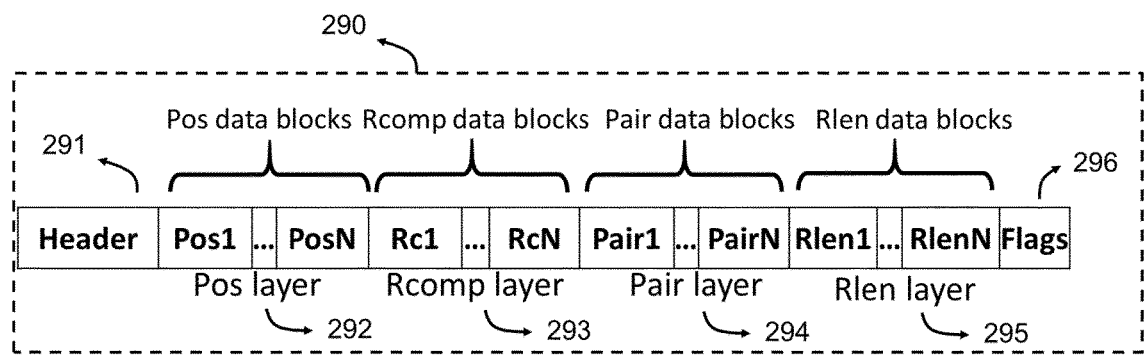

Figure 30 – Access units of type 1 contain data that refer to data carried by access units of type 0.

Type 2
An Access Unit of type 2 is composed by a header and the multiplexing of data blocks of type pos, rcomp, pair (optional), rlen (optional) and nmis
It is used to encode reads of class N

- Pos: reads position on the reference (1 per class)
- Rcomp: reverse compl. Flag (1 per class)
- Pair: (optional) pairing information (1 per class)
- Rlen: (optional) reads length in case of variable reads length
- Nmis: position of N mismatches

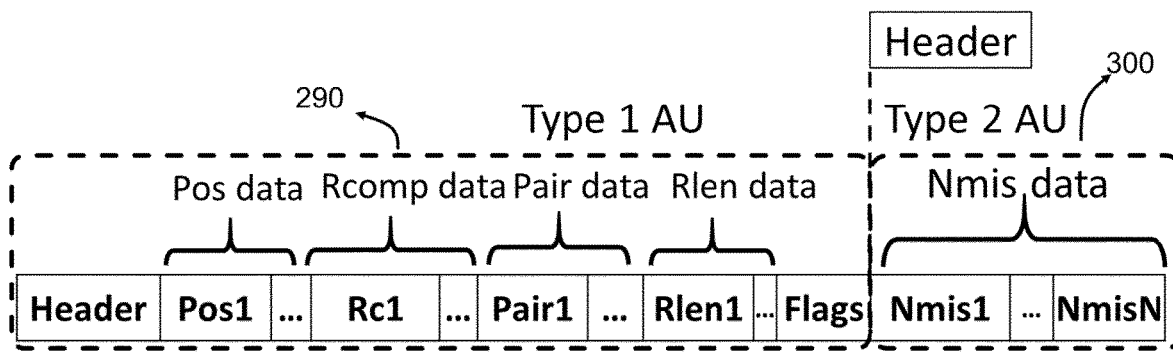

Figure 31 - Access units of type 2 contain data that refer to an access unit of type 1. These are the positions of N in the encoded reads.

Type 3
An Access Unit of type 3 is composed by a header and the multiplexing of data blocks of type pos, rcomp, pair (optional), rlen (optional), snpp, snpt
It is used to encode reads of class M

- Pos: reads position on the reference (1 per class)
- Rcomp: reverse compl. Flag (1 per class)
- Pair: (optional) pairing information (1 per class)
- Rlen: (optional) reads length in case of variable reads length
- Snpp: mismatch positions
- Snpt: mismatch type

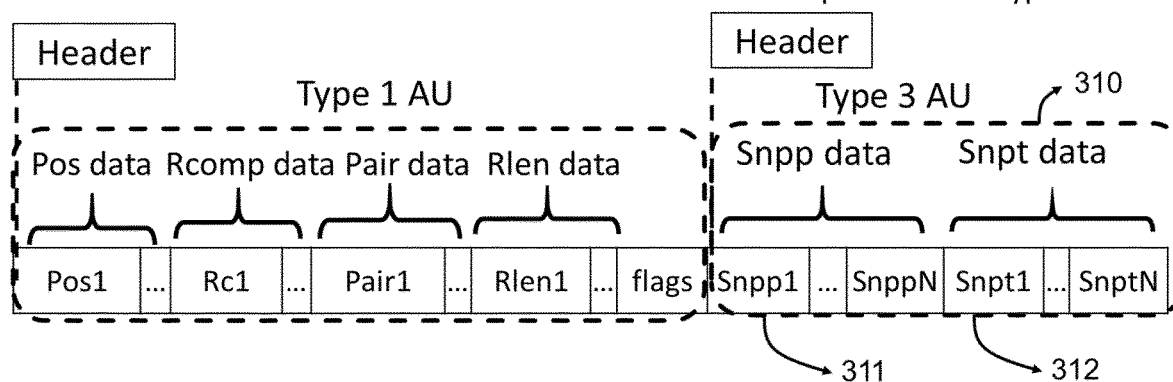

Figure 32 - Access units of type 3 contain data that refer to an access unit of type 1. These are the positions and types of mismatches in the encoded reads.

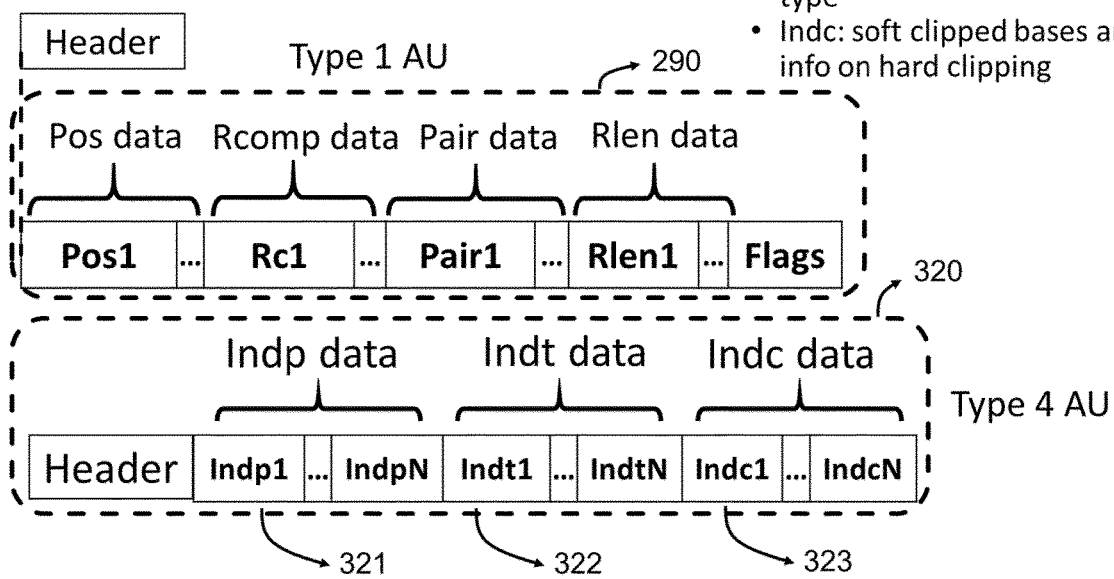
Figure 33 - Access units of type 4 contain data that refer to an access unit of type 1. These are the positions and types of mismatches in the encoded reads.

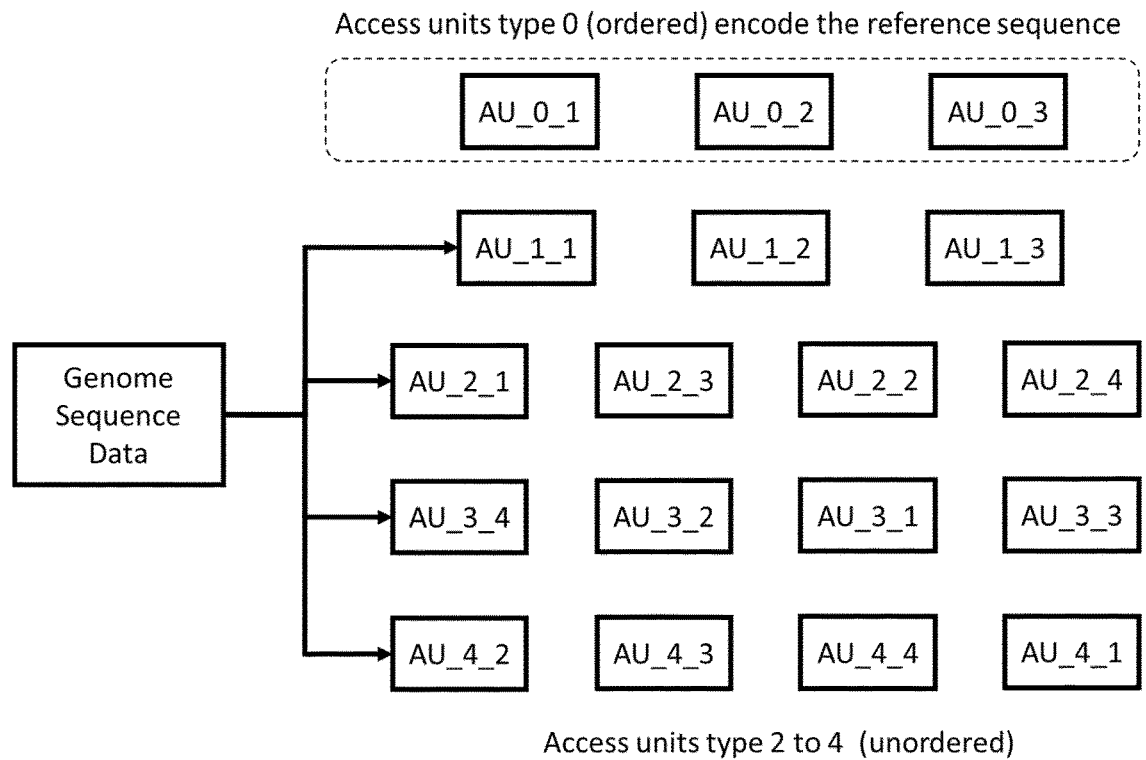
Figure 34 - The first five types of Access Units.
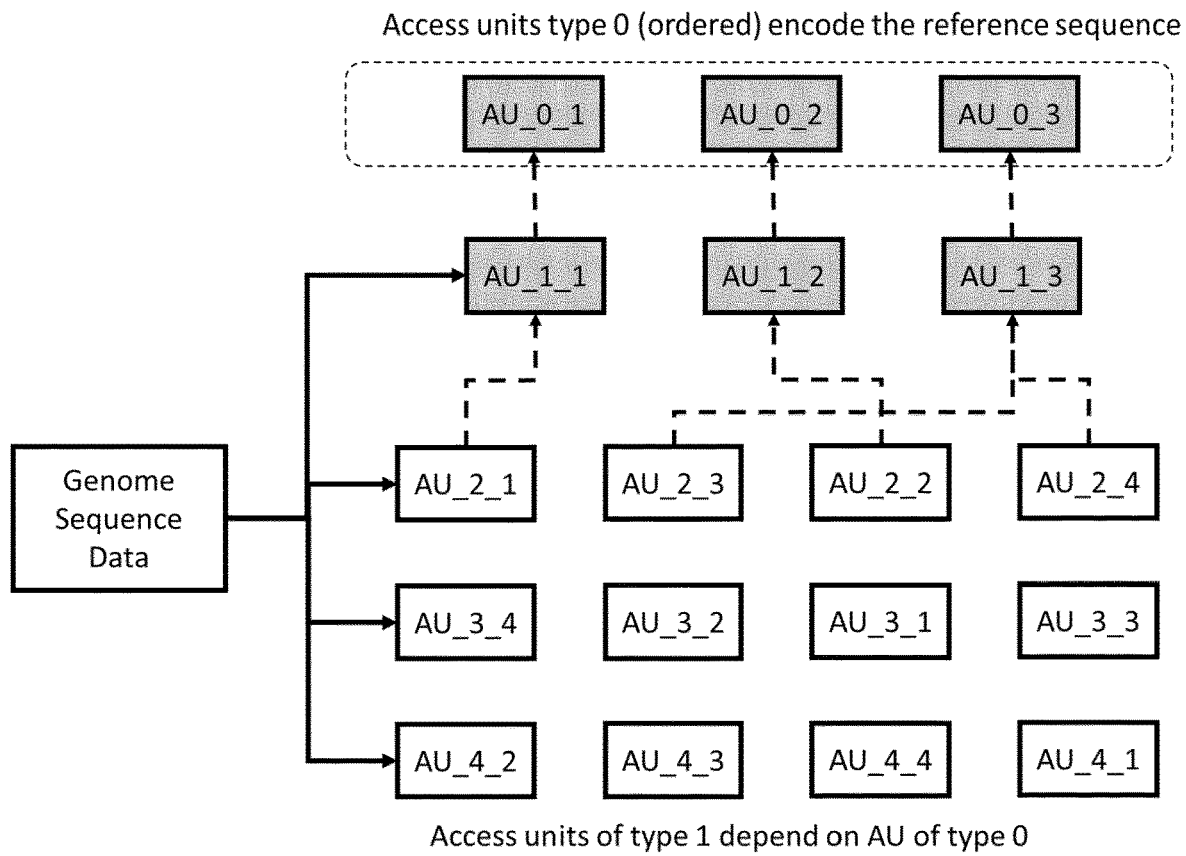
Figure 35 - Access Units of type 1 refer to Access Units of type 0 to be decoded.

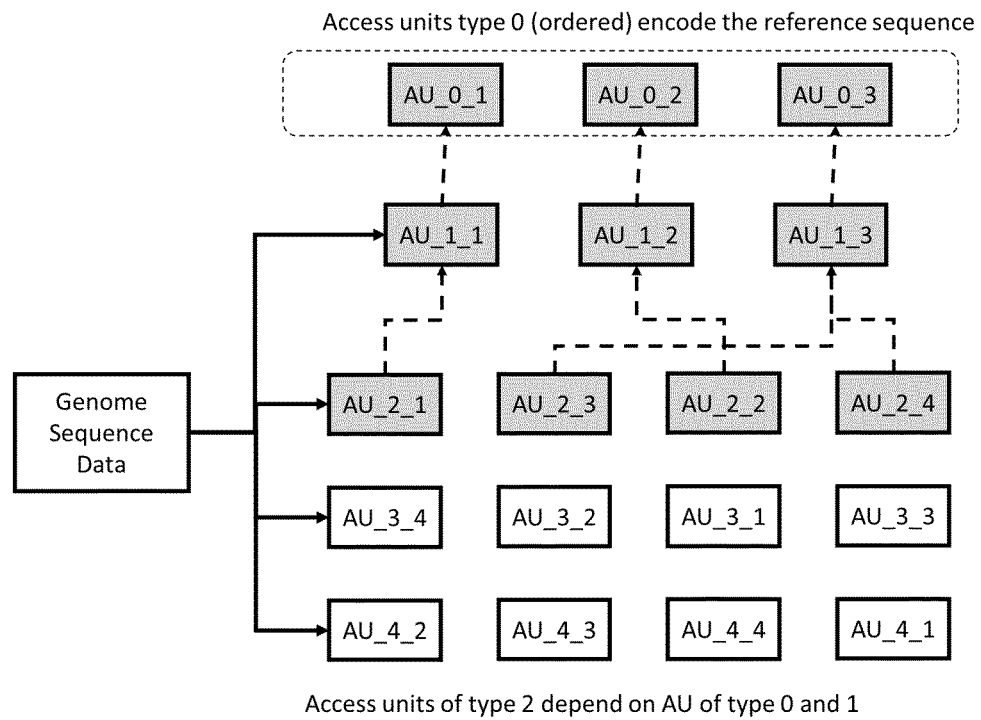
Figure 36 - Access Units of type 2 refer to Access Units of type 0 and 1 to be decoded.
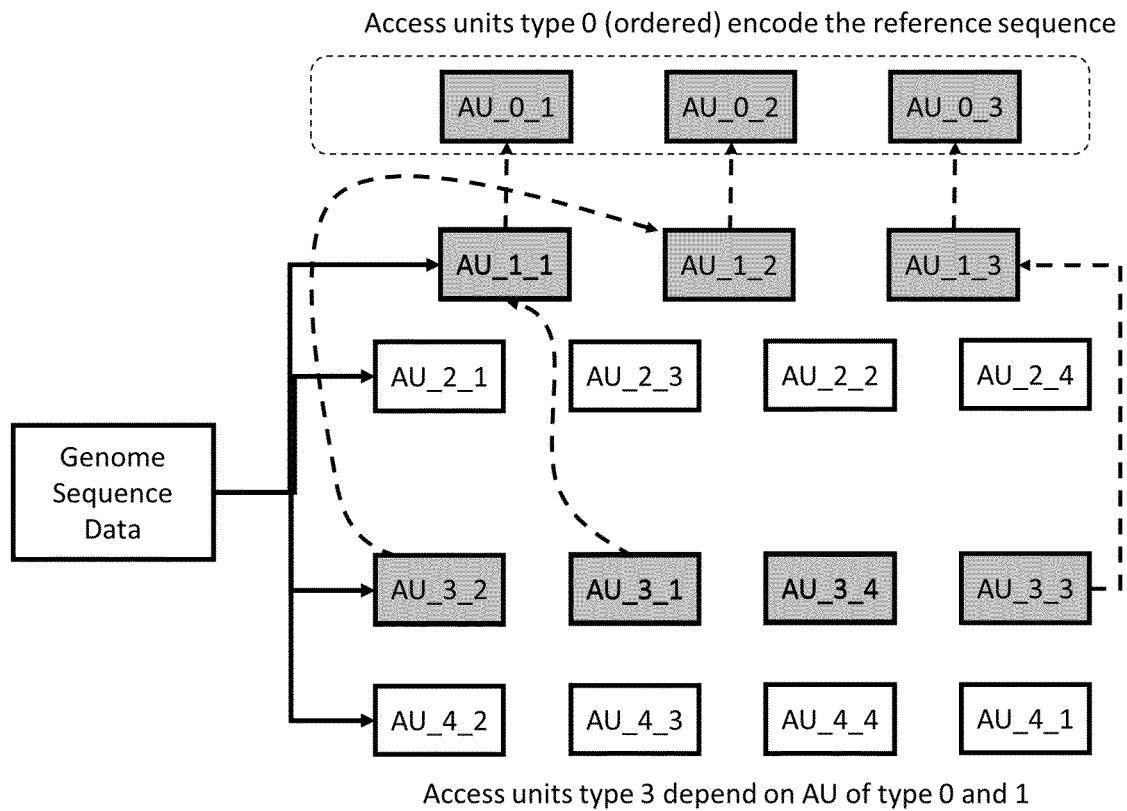
Figure 37 - Access Units of type 3 refer to Access Units of type 0 and 1 to be decoded.

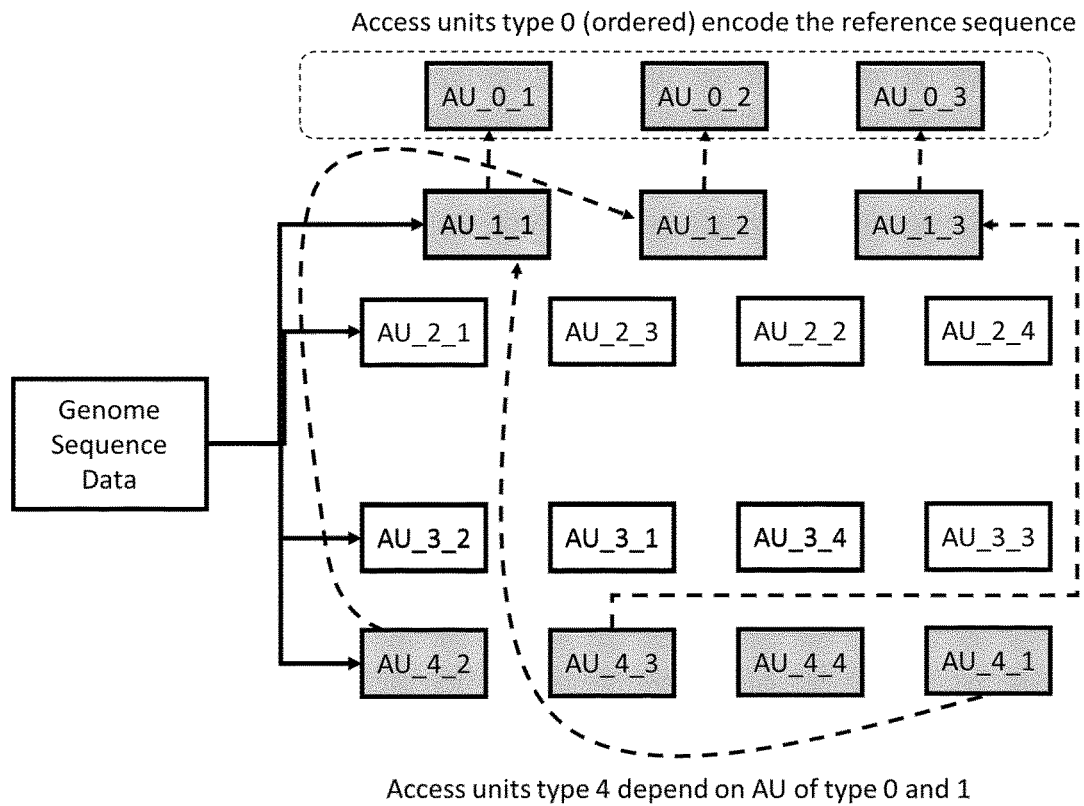
Figure 38 - Access Units of type 4 refer to AUs of type 1 to encode class I reads.
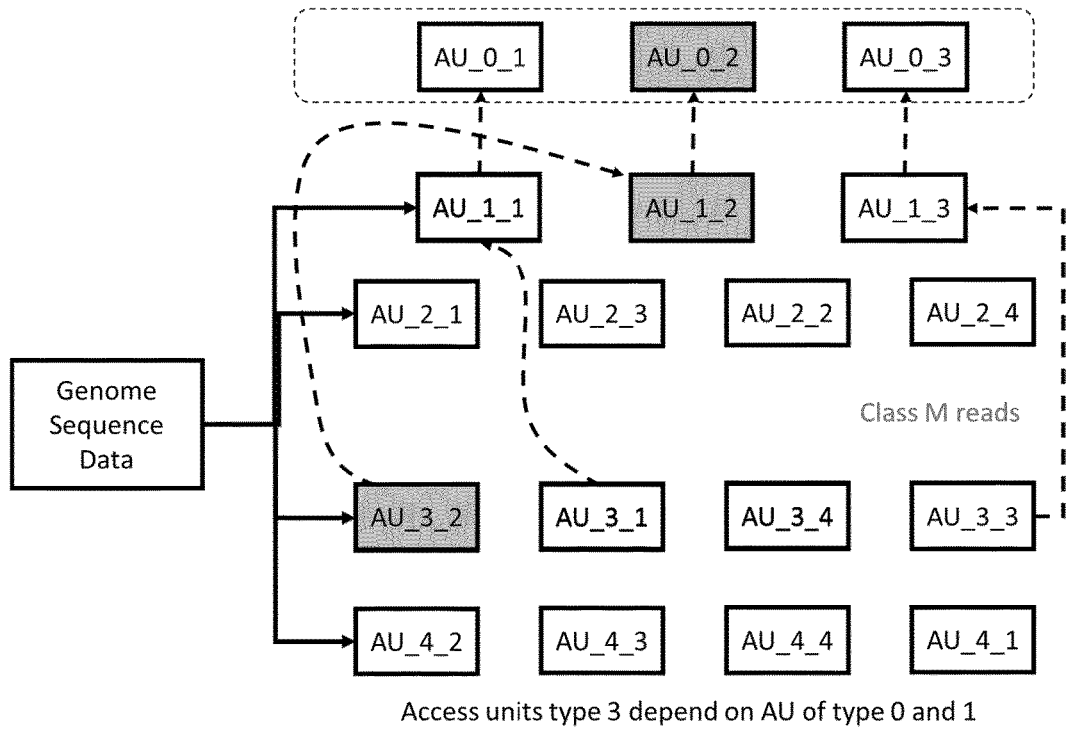
Figure 39 – Access Units required to decode sequence reads with mismatches mapped on the second segment of the reference sequence (AU 0-2).

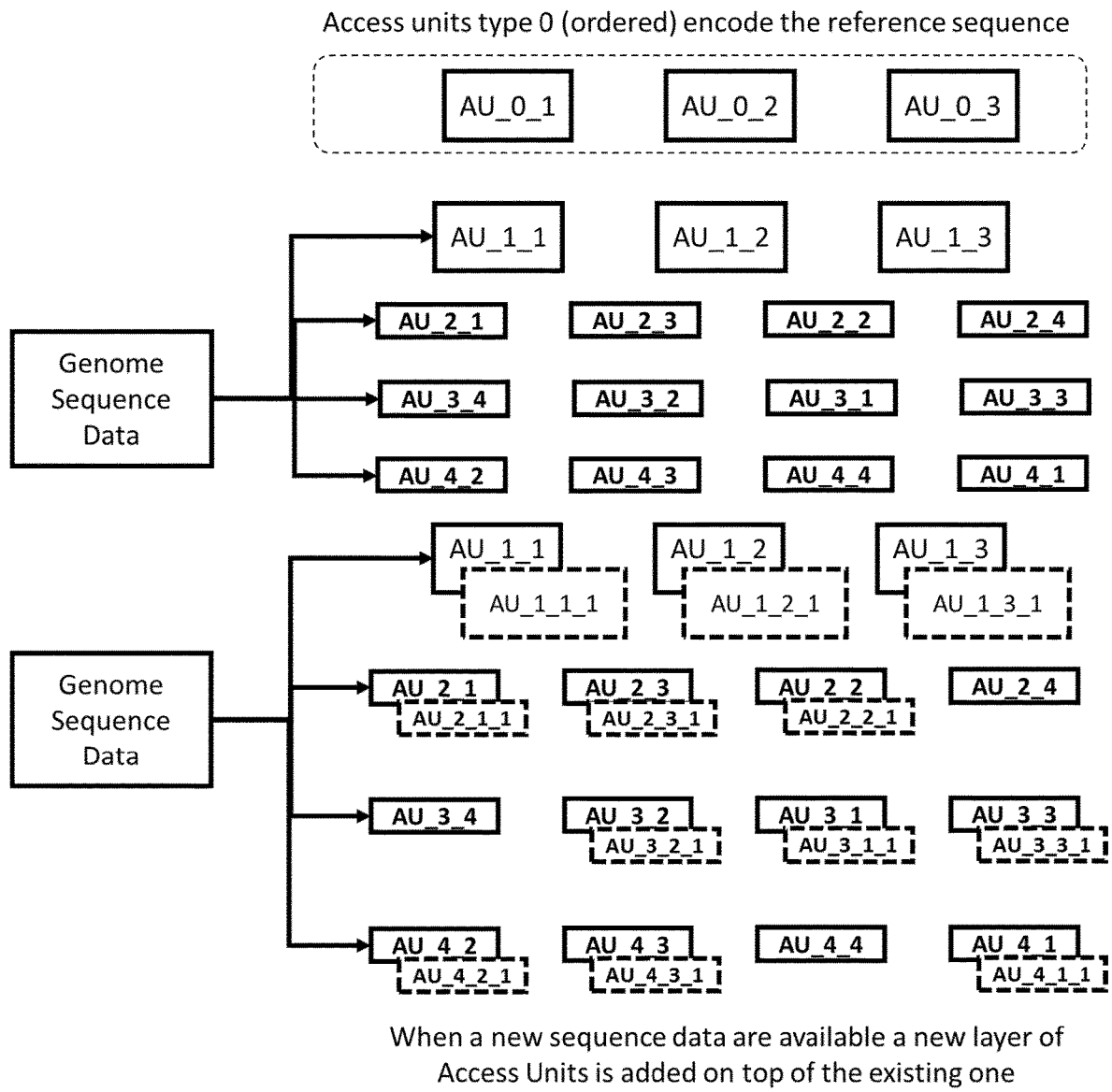
Figure 40 - When new data are available, a new layer of Access Units is built on top of the existing data.

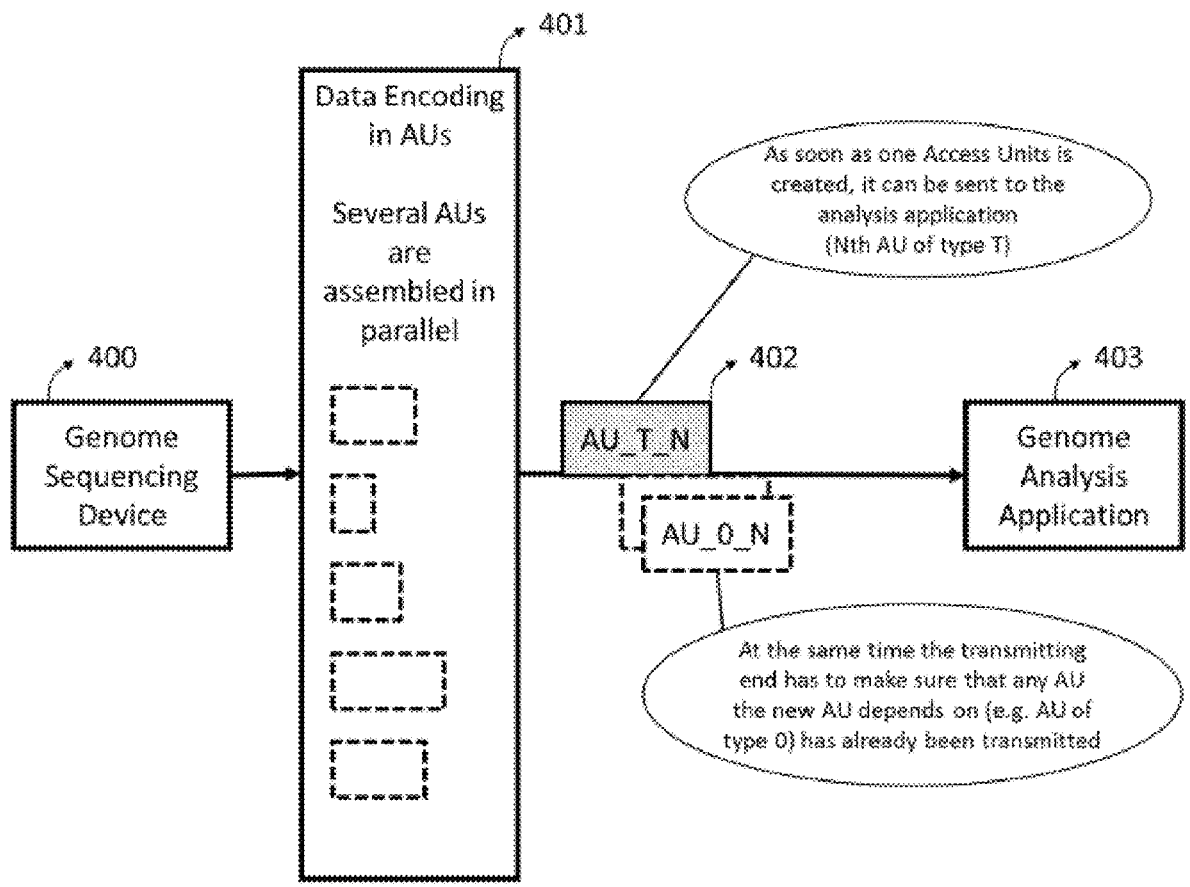
Figure 41 - A data structure based on Access Units enables genomic data analysis to start before the sequencing process is completed.
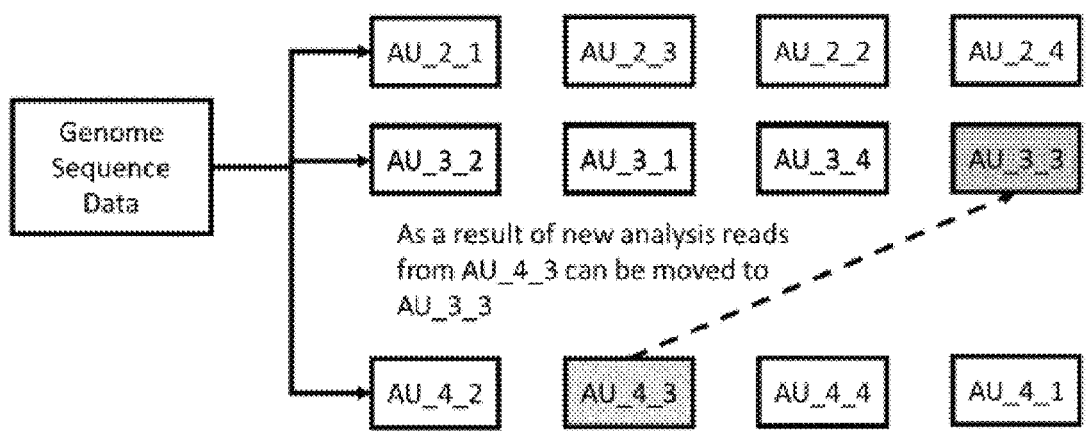
Figure 42 - New analysis performed on existing data may require moving reads from AUs of type 4 to one of type 3.

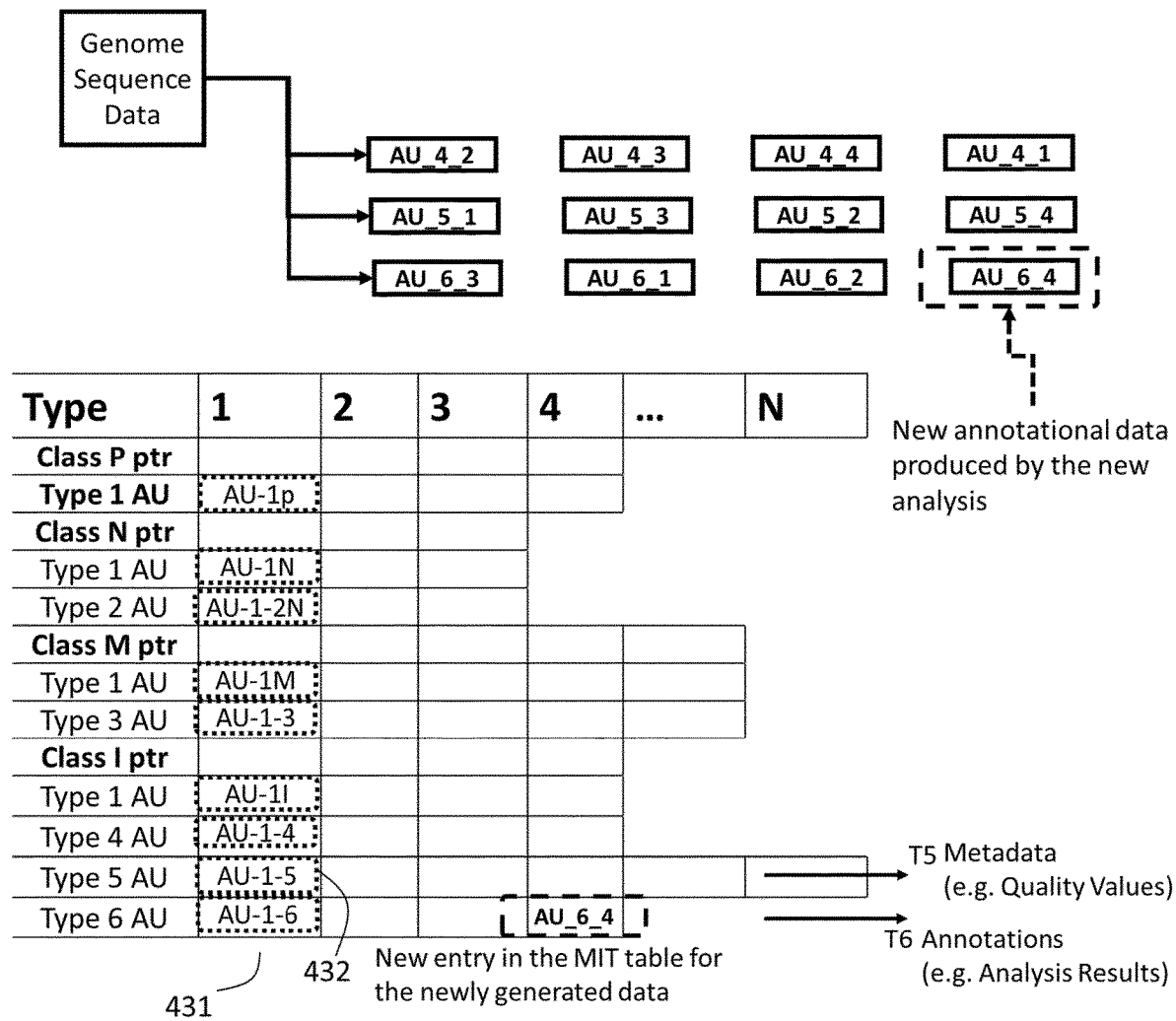
Figure 43 - Newly generated analysis data are encapsulated in a new AU of type 6 and a corresponding index is created in the MIT.

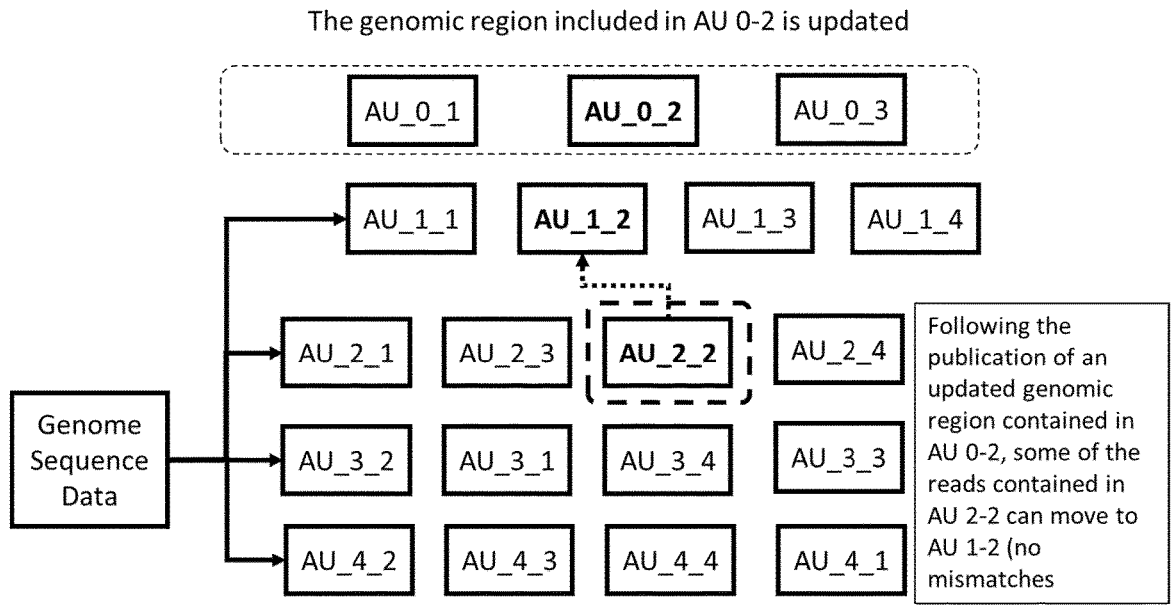
Figure 44 - Transcoding due to the publication of a new reference sequence (genome).
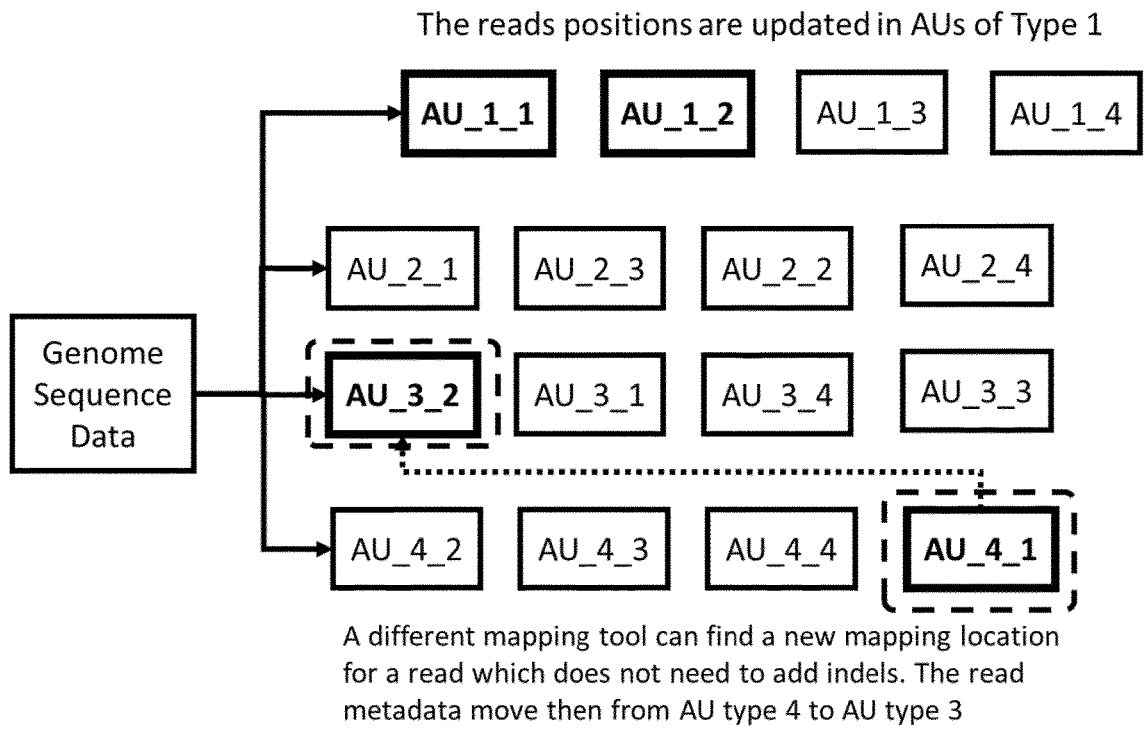
Figure 45 - Reads mapped to a new genomic region with better quality (e.g. no indels) are moved from AU of type 4 to AU of type 3.

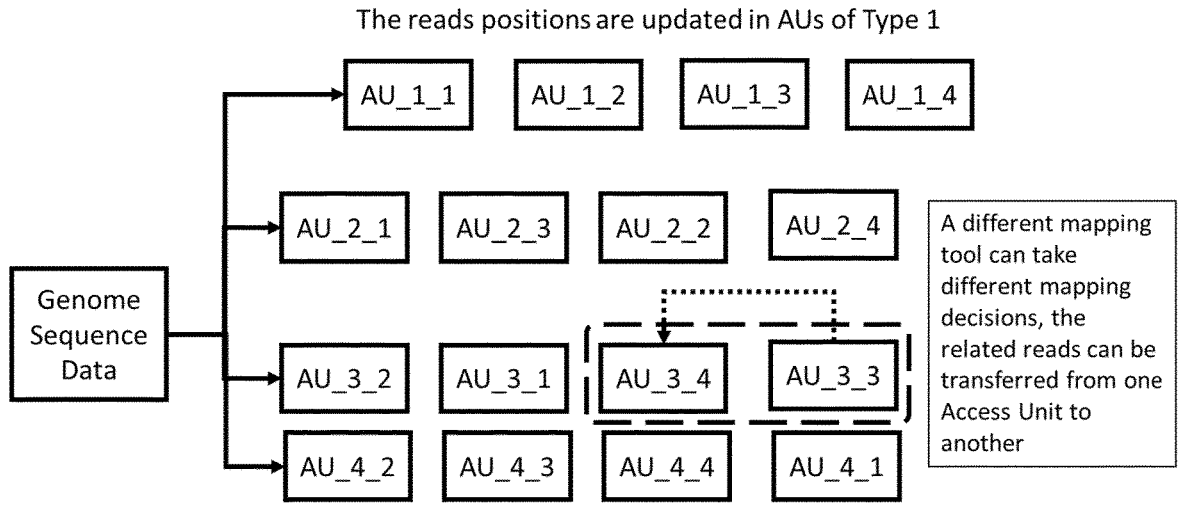
Figure 46 – In case new mapping location is found (e.g. with less mismatches) the related reads can be moved from one AU to another of the same type.
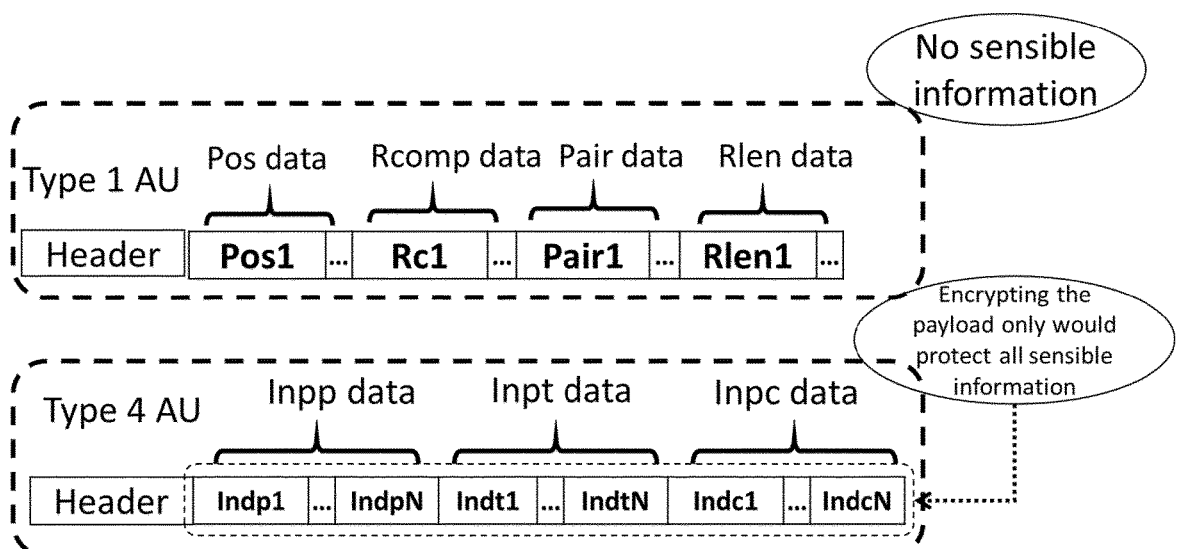
Figure 47 – Selective encryption can be applied on Access Units of Type 4 only as they contain the sensible information to be protected.

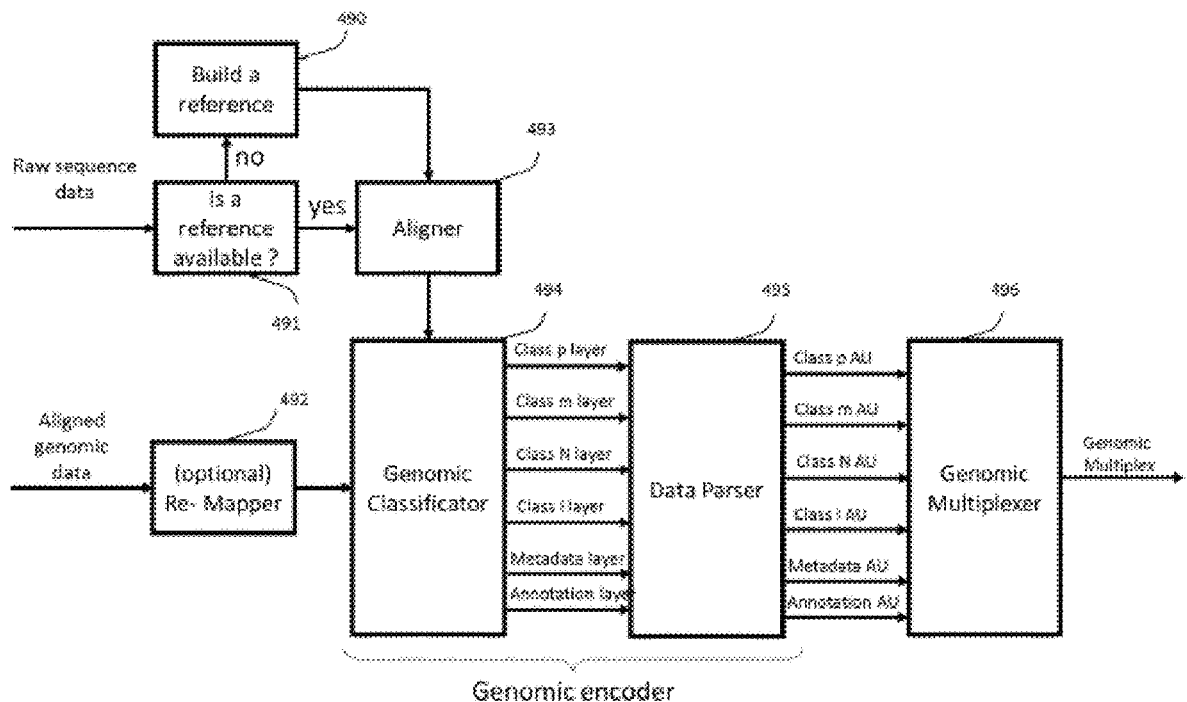

Figure 48 - The genomic encoder presents a first stage of data classification and a second of stage of data parsing and encoding. It can be preceded by alignment on an external or internally generated reference sequence. A genomic encoder can use aligners and de-novo assemblers to prepare data for encoding.

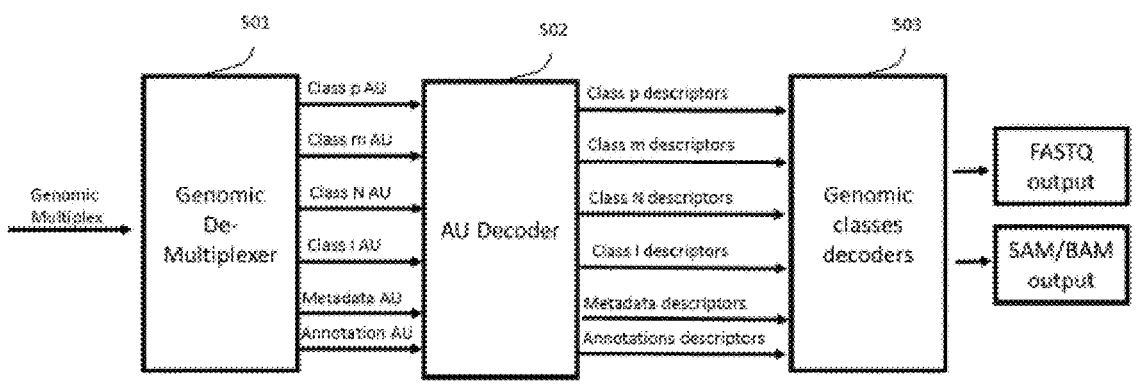

Figure 49 – A genomic demultiplexer extracts Access Units layers from the Genomic Multiplex, one decoder per AU type extracts the genomic descriptors which are then decoded into various genomic formats such as for example FASTQ and SAM/BAM

METHOD AND SYSTEM FOR STORING AND ACCESSING BIOINFORMATICS DATA

CROSS REFERENCE TO RELATED APPLICATIONS

This application is a U.S. National Phase patent application of PCT/EP2016/074301, filed Oct. 11, 2016, which is hereby incorporated by reference in the present disclosure in its entirety.

TECHNICAL FIELD

The present application provides new methods for efficient storing, access and transmission of bioinformatics data and in particular genomic sequencing data.

BACKGROUND

An appropriate representation of genome sequencing data is fundamental to enable efficient processing, storage and transmission of genomic data to render possible and facilitate analysis applications such as genome variants calling and all analysis performed, with various purposes, by processing the sequencing data and metadata. Today, genome sequencing information are generated by High Throughput Sequencing (HTS) machines in the form of sequences of nucleotides (a.k.a. bases) represented by strings of letters from a defined vocabulary.

These sequencing machines do not read out an entire genome or genes, but they produce short random fragments of nucleotide sequences known as sequence reads.

A quality score is associated to each nucleotide in a sequence read. Such number represents the confidence level given by the machine to the read of a specific nucleotide at a specific location in the nucleotide sequence.

This raw sequencing data generated by NGS machines are commonly stored in FASTQ files (see also FIG. 1).

The smallest vocabulary to represent sequences of nucleotides obtained by a sequencing process is composed by five symbols: {A, C, G, T, N} representing the 4 types of nucleotides present in DNA namely Adenine, Cytosine, Guanine, and Thymine plus the symbol N to indicate that the sequencing machine was not able to call any base with a sufficient level of confidence, so the type of base in such position remains undetermined in the reading process. In RNA Thymine is replaced by Uracil (U). The nucleotides sequences produced by sequencing machines are called "reads". In case of paired reads the term "template" is used to designate the original sequence from which the read pair has been extracted. Sequence reads can be composed by a number of nucleotides in a range from a few dozen up to several thousand. Some technologies produce sequence reads in pairs where each read can come from one of the two DNA strands.

In the genome sequencing field the term "coverage" is used to express the level of redundancy of the sequence data with respect to a reference genome. For example, to reach a coverage of 30× on a human genome (3.2 billion bases long) a sequencing machine shall produce a total of about 30×3.2 billion bases so that in average each position in the reference is "covered" 30 times.

State of the Art Solutions

The most used genome information representations of sequencing data are based on FASTQ and SAM file formats which are commonly made available in zipped form to reduce the original size. The traditional file formats, respectively FASTQ and SAM for non-aligned and aligned sequencing data, are constituted by plain text characters and are thus compressed by using general purpose approaches such as LZ (from Lem pel and Ziv, the authors who published the first versions) schemes (the well-known zip, gzip etc). When general purpose compressors such as gzip are used, the result of the compression is usually a single blob of binary data. The information in such monolithic form results quite difficult to archive, transfer and elaborate particularly in the case of high throughput sequencing when the volumes of data are extremely large.

After sequencing, each stage of a genomic information processing pipeline produces data represented by a completely new data structure (file format) despite the fact that in reality only a small fraction of the generated data is new with respect to the previous stage.

FIG. 1 shows the main stages of a typical genomic information processing pipeline with the indication of the associated file format representation.

Commonly used solutions presents several drawbacks: data archival is inefficient for the fact that a different file format is used at each stage of the genomic information processing pipelines which implies the multiple replication of data, with the consequent rapid increase of the required storage space. This is not efficient by itself because not logically necessary, but it is inefficient and unnecessary and it is also becoming not sustainable for the increase of the data volume generated by HTS machines. This has in fact consequences in terms of available storage space and generated costs, and it is also hindering the benefits of genomic analysis in healthcare from reaching a larger portion of the population. The impact of the IT costs generated by the exponential growth of sequence data to be stored and analysed is currently one of the main challenges the scientific community and that the healthcare industry have to face (see Scott D. Kahn "On the future of genomic data"—Science 331, 728 (2011) and Pavlichin, D. S., Weissman, T., and G. Yona. 2013. "The human genome contracts again" Bioinformatics 29(17): 2199-2202). At the same time several are the initiatives attempting to scale genome sequencing from a few selected individuals to large populations (see Josh P. Roberts "Million Veterans Sequenced"—Nature Biotechnology 31, 470 (2013))

The transfer of genomic data is slow and inefficient because the currently used data formats are organized into monolithic files of up to several hundred Gigabytes of size which need to be entirely transferred at the receiving end in order to be processed. This implies that the analysis of a small segment of the data requires the transfer of the entire file with significant costs in terms of consumed bandwidth and waiting time. Often online transfer is prohibitive for the large volumes of the data to be transferred, and the transport of the data is performed by physically moving storage media such as hard disk drives or storage servers from one location to another.

These limitations occurring when employing state of the art approaches are overcome by the present invention. Processing the data is slow and inefficient for to the fact that the information is not structured in such a way that the portions of the different classes of data and metadata required by commonly used analysis applications cannot be retrieved without the need of accessing the data in its totality. This fact implies that common analysis pipelines can require to run for days or weeks wasting precious and costly processing resources because of the need, at each stage of accessing, of parsing and filtering large volumes of data even if the portions of data relevant for the specific analysis purpose is much smaller.

These limitations are preventing health care professionals from timely obtaining genomic analysis reports and promptly reacting to diseases outbreaks. The present invention provides a solution to this need.

There is another technical limitation that is overcome by the present invention.

In fact the invention aims at providing an appropriate genomic sequencing data and metadata representation by organizing and partitioning the data so that the compression of data and metadata is maximized and several functionality such as selective access and support for incremental updates and many others are efficiently enabled.

A key aspect of the invention is a specific definition of classes of data and metadata to be represented by an appropriate source model, coded (i.e. compressed) separately by being structured in specific layers. The most important achievements of this invention with respect to existing state of the art methods consist in:

The increase of compression performance due to the reduction of the information source entropy constituted by providing an efficient model for each class of data or metadata;

the possibility of performing selective accesses to portions of the compressed data and metadata for any further processing purpose;

the possibility to incrementally (without the need of re-encoding) update and add encoded data and metadata with new sequencing data and/or metadata and/or new analysis results;

the possibility of efficiently process data as soon as they are produced by the sequencing machine or alignment tools without the need to wait the end of the sequencing or alignment process.

The present application discloses a method and system addressing the problem of efficient manipulation, storage and transmission of very large amounts of genomic sequencing data, by employing a structured access units approach.

The present application overcomes all the limitations of the prior art approaches related to the functionality of genomic data accessibility, efficient processing of data subsets, transmission and streaming functionality combined with an efficient compression.

Today the most used representation format for genomic data is the Sequence Alignment Mapping (SAM) textual format and its binary correspondent BAM. SAM files are human readable ASCII text files whereas BAM adopts a block based variant of gzip. BAM files can be indexed to enable a limited modality of random access. This is supported by the creation of a separate index file.

The BAM format is characterized by poor compression performance for the following reasons:
1. It focus on compressing the inefficient and redundant SAM file format rather than on extracting the actual genomic information conveyed by SAM files and using appropriate models for compressing it.
2. It employs a general purpose text compression algorithm such as gzip rather than exploiting the specific nature of each data source (the genomic information itself).
3. It lacks any concept related to data classification that would enable a selective access to specific classes of genomic data.

A more sophisticated approach to genomic data compression that is less commonly used, but more efficient than BAM is CRAM (CRAM specification: https://samtools.github.io/hts-specs/CRAMv3.pdf). CRAM provides a more efficient compression for the adoption of differential encoding with respect to an existing reference (it partially exploits the data source redundancy), but it still lacks features such as incremental updates, support for streaming and selective access to specific classes of compressed data.

CRAM relies on the concept of the CRAM record. Each CRAM record encodes a single mapped or unmapped reads by encoding all the elements necessary to reconstruct it.

The main differences of the disclosed invention with respect to the CRAM approach are:
1. For CRAM, data indexing is out of the scope of the specification (see section 12 of CRAM specification v 3.0) and it is implemented as a separate file. In the present invention the data indexing is integrated with the encoding process and indexes are embedded in the encoded bit stream.
2. In CRAM all core data blocks can contain any type of mapped reads (perfectly matching reads, reads with substitutions only, reads with indels). In the present invention there is no notion of classification and grouping of reads in classes according to the result of a mapping with respect to a reference sequence.
3. In the described invention there is no notion of record encapsulating each read because the data needed to reconstruct each read is scattered among several data containers called "layers". This enables a more efficient access to set of reads with specific biological characteristics (e.g. reads with substitutions, but without indels, or perfectly mapped reads) without the need of decoding each (block of) read(s) to inspect its features.
4. In a CRAM record each type of data is denoted by a specific flag. Differently from CRAM in the present invention there is no notion of flag denoting data because this is intrinsically defined by the "layer" the data belongs to. This implies a largely reduced number of symbols to be used and a consequent reduction of the information source entropy which results into a more efficient compression. This is due to the fact that the use of different "layers" enables the encoder to reuse the same symbol across each layer with different meanings. In CRAM each flag must always have the same meaning as there is no notion of contexts and each CRAM record can contain any type of data.
5. In CRAM substitutions, insertions and deletions are expressed according to different syntaxes, whereas the present invention uses a single alphabet and encoding for substitutions, insertions and deletions. This makes the encoding and decoding process simpler and produces a lower entropy source model which coding yields bit-streams characterized by higher compression performance.

Genomic compression algorithms used in the state of the art can be classified into these categories:
Transform-based
LZ-based
Read reordering
Assembly-based
Statistical modeling The first two categories share the disadvantage of not exploiting the specific characteristics of the data source (genomic sequence reads) and process the genomic data as string of text to be compressed without taking into account the specific properties of such kind of information (e.g. redundancy among reads, reference to an existing sample). Two of the most advanced toolkits for genomic data compression, namely CRAM and Goby ("Compression of structured high-throughput sequencing data", F. Campagne, K. C. Dorff, N. Chambwe, J. T. Robinson, J. P. Mesirov, T. D. Wu), make a poor use of arithmetic coding as they implicitly model data as independent and identically distributed by a Geometric distribution. Goby is slightly more sophisticated since it converts all the fields to a list of integers and each list is encoded independently using arithmetic coding without using any context. In the most efficient mode of operation, Goby is able to perform some inter-list modeling over the integer lists to improve compression. These prior art solutions yield poor compression ratios and data structures that are difficult if not impossible to selectively access and manipulate once compressed. Downstream analysis stages can result to be inefficient and very slow due to the necessity of handling large and rigid data structures even to perform simple operation or to access selected regions of the genomic dataset.

A simplified vision of the relation among the file formats used in genome processing pipelines is depicted in FIG. 1. In this diagram file inclusion does not imply the existence of a nested file structure, but it only represents the type and amount of information that can be encoded for each format (i.e. SAM contains all information in FASTQ, but organized in a different file structure). CRAM contains the same genomic information as SAM/BAM, but it has more flexibility in the type of compression that can be used, therefore it is represented as a superset of SAM/BAM.

The use of multiple file formats for the storage of genomic information is highly inefficient and costly. Having different file formats at different stages of the genomic information life cycle implies a linear growth of utilized storage space even if the incremental information is minimal. Further disadvantages of prior art solutions are listed below.

1. Accessing, analysing or adding annotations (metadata) to raw data stored in compressed FastQ files or any combination thereof requires the decompression and recompression of the entire file with extensive usage of computational resources and time.
2. Retrieving specific subsets of information such as read mapping position, read variant position and type, indels position and types, or any other metadata and annotation contained in aligned data stored in BAM files requires to access the whole data volume associated to each read. Selective access to a single class of metadata is not possible with prior art solutions.
3. Prior art file formats require that the whole file is received at the end user before processing can start. For example the alignment of reads could start before the sequencing process has been completed relying on an appropriate data representation. Sequencing, alignment and analysis could proceed and run in parallel.
4. Prior art solutions do not support structuring and are not able of distinguishing genomic data obtained by different sequencing processes according to their specific generation semantic (e.g. sequencing obtained at different time of the life of the same individual). The same limitation occurs for sequencing obtained by different types of biological samples of the same individual.
5. The encryption of entire or selected portions of the data is not supported by prior art solutions. For example the encryption of:
    a. selected DNA regions
    b. only those sequences containing variants
    c. chimeric sequences only
    d. unmapped sequences only
    e. specific metadata (e.g. origin of the sequenced sample, identity of sequenced individual, type of sample)
6. The transcoding from sequencing data aligned to a given reference (i.e. a SAM/BAM file) to a new reference requires to process the entire data volume even if the new reference differs only by a single nucleotide position from the previous reference.

There is therefore a need of an appropriate Genomic Information Storage Layer (Genomic File Format) that enables efficient compression, supports the selective access in the compressed domain, supports the incremental addition of heterogeneous metadata in the compressed domain at all levels of the different stages of the genomic data processing.

The present invention provides a solution to the limitations of the state of the art by employing the method, devices and computer programs as claimed in the accompanying set of claims.

LIST OF FIGURES

FIG. 1 shows the main steps of a typical genomic pipeline and the related file formats.

FIG. 2 shows the mutual relationship among the most used genomic file formats

FIG. 3 shows how genomic sequence reads are assembled in an entire or partial genome via de-novo assembly or reference based alignment.

FIG. 4 shows how reads mapping positions on the reference sequence are calculated.

FIG. 5 shows how reads pairing distances are calculated.

FIG. 6 shows how pairing errors are calculated.

FIG. 7 shows how the pairing distance is encoded when a read mate pair is mapped on a different chromosome.

FIG. 8 shows how sequence reads can come from the first or second DNA strand of a genome.

FIG. 9 shows how a read mapped on strand 2 has a corresponding reverse complemented read on strand 1.

FIG. 10 shows the four possible combinations of reads composing a reads pair and the respective encoding in the rcomp layer.

FIG. 11 shows how N mismatches are encoded in a nmis layer.

FIG. 12 shows an example of substitutions in a mapped read pair.

FIG. 13 shows how substitutions positions can be calculated either as absolute or differential values.

FIG. 14 shows how symbols encoding substitutions without IUPAC codes are calculated.

FIG. 15 shows how substitution types are encoded in the snpt layer.

FIG. 16 shows how symbols encoding substitutions with IUPAC codes are calculated.

FIG. 17 shows an alternative source model for substitution where only positions are encoded, but one layer per substitution type is used.

FIG. 18 shows how to encode substitutions, inserts and deletions in a reads pair of class I when IUPAC codes are not used.

FIG. 19 shows how to encode substitutions, inserts and deletions in a reads pair of class I when IUPAC codes are used.

FIG. 20 shows the structure of the header of the genomic information data structure.

FIG. 21 shows how the Master Index Table contains the positions on the reference sequences of the first read in each Access Unit.

FIG. 22 shows an example of partial MIT showing the mapping positions of the first read in each pos AU of class P.

FIG. 23 shows how the Local Index Table in the layer header is a vector of pointers to the AUs in the payload.

FIG. 24 shows an example of Local Index Table.

FIG. 25 shows the functional relation between Master Index Table and Local Index Tables.

FIG. 26 shows how Access Units are composed by blocks of data belonging to several layers. Layers are composed by Blocks subdivided in Packets.

FIG. 27 shows how a Genomic Access Unit of type 1 (containing positional, pairing, reverse complement and read length information) is packetized and encapsulated in a Genomic Data Multiplex.

FIG. 28 shows how Access Units are composed by a header and multiplexed blocks belonging to one or more layers of homogeneous data. Each block can be composed by one or more packets containing the actual descriptors of the genomic information.

FIG. 29 shows the structure of Access Units of type 0 which do not need to refer to any information coming from other access units to be accessed or decoded and accessed.

FIG. 30 shows the structure of Access Units of type 1.

FIG. 31 shows the structure of Access Units of type 2 which contain data that refer to an access unit of type 1. These are the positions of N in the encoded reads.

FIG. 32 shows the structure of Access Units of type 3 which contain data that refer to an access unit of type 1. These are the positions and types of mismatches in the encoded reads.

FIG. 33 shows the structure of Access Units of type 4 which contain data that refer to an access unit of type 1. These are the positions and types of mismatches in the encoded reads.

FIG. 34 shows the first five type of Access Units.

FIG. 35 shows that Access Units of type 1 refer to Access Units of type 0 to be decoded.

FIG. 36 shows that Access Units of type 2 refer to Access Units of type 0 and 1 to be decoded.

FIG. 37 shows that Access Units of type 3 refer to Access Units of type 0 and 1 to be decoded.

FIG. 38 shows that Access Units of type 4 refer to Access Units of type 0 and 1 to be decoded.

FIG. 39 shows the Access Units required to decode sequence reads with mismatches mapped on the second segment of the reference sequence (AU 0-2).

FIG. 40 shows how raw genomic sequence data that becomes available can be incrementally added to pre-encoded genomic data.

FIG. 41 shows how a data structure based on Access Units enables genomic data analysis to start before the sequencing process is completed.

FIG. 42 shows how new analysis performed on existing data can imply that reads are moved from AUs of type 4 to one of type 3.

FIG. 43 shows how newly generated analysis data are encapsulated in a new AU of type 6 and a corresponding index is created in the MIT.

FIG. 44 shows how to transcode data due to the publication of a new reference sequence (genome).

FIG. 45 shows how reads mapped to a new genomic region with better quality (e.g. no indels) are moved from AU of type 4 to AU of type 3.

FIG. 46 shows how, in case new mapping location is found, (e.g. with less mismatches) the related reads can be moved from one AU to another of the same type.

FIG. 47 shows how selective encryption can be applied on Access Units of Type 4 only as they contain the sensible information to be protected.

FIG. 48 shows how raw genomic sequence data or aligned genomic data are processed to be encapsulated in a Genomic Multiplex. The alignment, re-alignment, assembly stages can be necessary to prepare the data for encoding. The generated layers are encapsulated in Access Units and multiplexed by the Genomic Multiplexer FIG. 49 shows how a genomic demultiplexer (501) extracts Access Units layers from the Genomic Multiplex, one decoder per AU type (502) extracts the genomic descriptors which are then decoded (503) into various genomic formats such as for example FASTQ and SAM/BAM.

SUMMARY OF THE INVENTION

Various aspects, advantageous features and preferred embodiments of the present invention as summarized in the following items, respectively alone or in combination, contribute to solving the object of the invention:

(1) A method of partitioning a file of genomic data into access units of different types based on the predictability of said genomic data,
  said access units comprising genomic data related to
  positional information of reads of the genomic data and
  reverse complement information of said reads,
  wherein said predictability is such that
  access units of a first type contain genomic data that do not refer to access units of any other type and the access units of a second type contain information related to the access unit of a first type and additional information related to mismatching information with respect to the information contained in the access unit of a first type.

(2) The method of item (1), wherein said mismatching information are reads position and reverse complement information.

(3) The method of item (2), wherein said access units of a second type further comprise information related to pairing and/or further information related to reads length.

(4) The method of any preceding items wherein the said partitioning the genomic data into access units of different types further comprises an additional type of access unit containing information related to positions of mismatches where the sequencing machine was not able to determine any nucleotide.

(5) The method of any preceding items wherein the said partitioning the genomic data into access units of different types further comprises an additional type of access unit containing information related to mismatch position and mismatch type, said mismatch relating to information related to the access unit of the first type.

(6) The method of any preceding items wherein the said partitioning the genomic data into access units of different types further comprises an additional type of access unit containing information related to indels and mismatches position, indels and mismatches type and information on soft clipped nucleotides and info on hard clipping nucleotides.

(7) The method of any preceding items wherein the partitioning further comprises access units of another different type comprising information related metadata and/or quality scores and/or annotational data associated to the access unit of the second type, third type, fourth type or fifth type.

(8) The method of item (7) wherein the partitioning further comprises access units of an additional different type that comprises annotational data.

(9) The method of item (8) wherein the data of the access unit of any preceding items are organized into layers, each layer comprising information related to a different category: positional data, reverse complement, optionally paring, optionally mismatching and optionally annotational data.

(10) The method of any preceding items wherein the access units contain a header and payload data.

(11) The method of item (2) wherein the access unit of second type comprises information about pairing of the reads and wherein the presence of such information is signalled in the header of the access unit.

(12) The method of any preceding items wherein the number of reads comprised in an access unit of a first type is set by an input configuration parameter.

(13) The method of item (9) wherein said input configuration parameter is stored in the header of the access unit.

(14) The method of any preceding item where the content of the access units is encrypted.

(15) The method of item (14) wherein the encryption is limited to access units of type 3 and type 4.

(16) Apparatus comprising means suitable for carrying out the method of items (1)-(15).

(17) Support data storing genomic data partitioned into access units according to the method of items (1)-(15).

(18) A computer readable recording medium having recorded thereon a program comprising instruction set for executing the method of items (1)-(15).

(19) A file format storing genomic data partitioned into access units according to the method of items (1)-(15).

(20) A method of transcoding a file of genomic data partitioned into access units created according to the method of items (1)-(15), characterized in that only the payload information of the access data is modified, without having to transcode the entire file.

(21) The method of item (20), wherein the file structure is left unaltered.

(22) The method of item (21) wherein only selected access units are modified.

(23) The method of item (22) wherein the selected access units are of type 0.

(24) The method of item (23) wherein the selected access units are of any type 1-5.

DETAILED DESCRIPTION

The present invention describes a multiplexing file format and the relevant access units to be used to store, transport, access and process genomic or proteomic information in the form of sequences of symbols representing molecules.

These molecules include, for example, nucleotides, amino acids and proteins. One of the most important pieces of information represented as sequence of symbols are the data generated by high-throughput genome sequencing devices.

The genome of any living organism is usually represented as a string of symbols expressing the chain of nucleic acids (bases) characterizing that organism. Current state of the art genome sequencing technology is able to produce only a fragmented representation of the genome in the form of several (up to billions) strings of nucleic acids associated to metadata (identifiers, level of accuracy etc.). Such strings are usually called "sequence reads" or "reads".

The typical steps of the genomic information life cycle comprise Sequence reads extraction, Mapping and Alignment, Variant detection, Variant annotation and Functional and Structural Analysis (see FIG. 1).

Sequence reads extraction is the process—performed by either a human operator or a machine—of representation of fragments of genetic information in the form of sequences of symbols representing the molecules composing a biological sample. In the case of nucleic acids such molecules are called "nucleotides". The sequences of symbols produced by the extraction are commonly referred to as "reads". This information is usually encoded in prior art as FASTA files including a textual header and a sequence of symbols representing the sequenced molecules.

When the biological sample is sequenced to extract DNA of a living organism the alphabet is composed by the symbols (A,C,G,T,N).

When the biological sample is sequenced to extract RNA of a living organism the alphabet is composed by the symbols (A,C,G,U,N).

In case the IUPAC extended set of symbols, so called "ambiguity codes" are also generated by the sequencing machine, the alphabet used for the symbols composing the reads are (A, C, G, T, U, W, S, M, K, R, Y, B, D, H, V, N or -).

When the IUPAC ambiguity codes are not used, a sequence of quality score can be associated to each sequence read. In such case prior art solutions encode the resulting information as a FASTQ file. Sequencing devices can introduce errors in the sequence reads such as:

1. identification of a wrong symbol (i.e. representing a different nucleic acid) to represent the nucleic acid actually present in the sequenced sample; this is usually called "substitution error" (mismatch);
2. insertion in one sequence read of additional symbols that do not refer to any actually present nucleic acid; this is usually called "insertion error";
3. deletion from one sequence read of symbols that represent nucleic acids that are actually present in the sequenced sample; this is usually called "deletion error";
4. recombination of one or more fragments into a single fragment which does not reflect the reality of the originating sequence.

The term "coverage" is used in literature to quantify the extent to which a reference genome or part thereof can be covered by the available sequence reads. Coverage is said to be:

partial (less than 1×) when some parts of the reference genome are not mapped by any available sequence read single (1×) when all nucleotides of the reference genome are mapped by one and only one symbol present in the sequence reads multiple (2×, 3×, N×) when each nucleotide of the reference genome is mapped multiple times.

Sequence alignment refers to the process of arranging sequence reads by finding regions of similarity that may be a consequence of functional, structural, or evolutionary relationships among the sequences. When the alignment is performed with reference to a pre-existing nucleotides sequence referred to as "reference genome", the process is called "mapping". Sequence alignment can also be performed without a pre-existing sequence (i.e. reference genome) in such cases the process is known in prior art as "de novo" alignment. Prior art solutions store this information in SAM, BAM or CRAM files. The concept of aligning sequences to reconstruct a partial or complete genome is depicted in FIG. 3.

Variant detection (a.k.a. variant calling) is the process of translating the aligned output of genome sequencing machines, (sequence reads generated by NGS devices and aligned), to a summary of the unique characteristics of the organism being sequenced that cannot be found in other pre-existing sequence or can be found in a few pre-existing sequences only. These characteristics are called "variants" because they are expressed as differences between the genome of the organism under study and a reference genome. Prior art solutions store this information in a specific file format called VCF file.

Variant annotation is the process of assigning functional information to the genomic variants identified by the process of variant calling. This implies the classification of variants according to their relationship to coding sequences in the genome and according to their impact on the coding sequence and the gene product. This is in prior art usually stored in a MAF file.

The process of analysis of DNA (variant, CNV=copy number variation, methylation etc,) strands to define their relationship with genes (and proteins) functions and structure is called functional or structural analysis. Several different solutions exist in the prior art for the storage of this data.

Genomic File Format

The invention disclosed in this document consists in the definition of a compressed data structure for representing, processing manipulating and transmitting genome sequencing data that differs from prior art solutions for at least the following aspects:

- It does not rely on any prior art representation formats of genomic information (i.e. FASTQ, SAM).
- It implements a new original classification of the genomic data and metadata according to their specific characteristics. Sequence reads are mapped to a reference sequence and grouped in distinct classes according to the results of the alignment process. This results in data classes with lower information entropy that can be more efficiently encoded applying different specific compression algorithms.
- It defines syntax elements and the related encoding/decoding process conveying the sequence reads and the alignment information into a representation which is more efficient to be processed for downstream analysis applications.

Classifying the reads according to the result of mapping and coding them using descriptors to be stored in layers (position layer, mate distance layer, mismatch type layer etc,) present the following advantages:

- A reduction of the information entropy when the different syntax elements are modelled by a specific source model.
- A more efficient access to data that are already organized in groups/layers that have a specific meaning for the downstream analysis stages and that can be accesses separately and independently.
- The presence of a modular data structure that can be updated incrementally by accessing only the required information without the need of decoding the whole data content.
- The genomic information produced by sequencing machines is intrinsically highly redundant due to the nature of the information itself and to the need of mitigating the errors intrinsic in the sequencing process. This implies that the relevant genetic information which needs to be identified and analyzed (the variations with respect to a reference) is only a small fraction of the produced data. Prior art genomic data representation formats are not conceived to "isolate" the meaningful information at a given analysis stage from the rest of the information so as to make it promptly available to the analysis applications.
- The solution brought by the disclosed invention is to represent genomic data in such a way that any relevant portion of data is readily available to the analysis applications without the need of accessing and decompressing the entirety of data and the redundancy of the data is efficiently reduced by efficient compression to minimize the required storage space and transmission bandwidth.

The key elements of the invention are:

1. The specification of a file format that "contains" structured and selectively accessible data elements Access Units (AU) in compressed form. Such approach can be seen as the opposite of prior art approaches, SAM and BAM for instance, in which data are structured in non-compressed form and then the entire file is compressed. A first clear advantage of the approach is to be able to efficiently and naturally provide various forms of structured selective access to the data elements in the compressed domain which is impossible or extremely awkward in prior art approaches.
2. The structuring of the genomic information into specific "layers" of homogeneous data and metadata presents the considerable advantage of enabling the definition of different models of the information sources characterized by low entropy. Such models not only can differ from layer to layer, but can also differ inside each layer when the compressed data within layers are partitioned into Data Blocks included into Access Units. This structuring enables the use of the most appropriate compression for each class of data or metadata and portion of them with significant gains in coding efficiency versus prior art approaches.
3. The information is structured in Access Units (AU) so that any relevant subset of data used by genomic analysis applications is efficiently and selectively accessible by means of appropriate interfaces. These features enable faster access to data and yield a more efficient processing.
4. The definition of a Master Index Table and Local Index Tables enabling selective access to the information carried by the layers of encoded (i.e. compressed) data without the need to decode the entire volume of compressed data.
5. The possibility of performing realignment of already aligned and compressed genomic data when it needs to be re-aligned versus newly published reference genomes by performing an efficient transcoding of selected data portions in the compressed domain. The frequent release of new reference genomes currently requires resource consuming and time for the transcoding processes to re-align already compressed and stored genomic data with respect to the newly published references because all data volume need to be processed.

The method described in this document aims at exploiting the available a-priori knowledge on genomic data to define an alphabet of syntax elements with reduced entropy. In genomics the available knowledge is represented by an existing genomic sequence usually—but not necessarily—of the same species as the one to be processed. As an example, human genomes of different individuals differ only of a fraction of 1%. On the other hand that small amount of data contain enough information to enable early diagnosis, personalized medicine, customized drugs synthesis etc. This invention aims at defining a genomic information representation format where the relevant information is efficiently accessible and transportable and the weight of the redundant information is reduced.

The technical features used in the present invention are:
1. Decomposition of the genomic information into "layers" of homogeneous metadata in order to reduce the information entropy as much as possible;
2. Definition of a Master Index Table and Local Index Tables to enable selective access to the layers of encoded information without the need to decode the entire coded information;
3. Adoption of context adaptive binary arithmetic coding to encode the syntax elements defined at point 1;
4. Synchronization of the layers to enable selective access to the data without the need to decode all the layers if not needed;
5. Differential encoding with respect to one or more adaptive reference sequences that can be modified to reduce entropy. After a first reference based encoding, the recorded mismatches can be used to "adapt/modify" the reference sequences in order to further reduce the information entropy. This is a process that can be performed iteratively as long as the reduction of information entropy is meaningful.

In order to solve all the aforementioned problems of the prior art (in terms of efficient access to random positions in the file, efficient transmission and storing, efficient compression) the present application re-orders and packs together the data that are more homogeneous and or semantically significant for the easiness of processing.

The present invention also adopts a data structure based on the concept of Access Unit.

Genomic data are structured and encoded into different access units. Hereafter follows a description of the genomic data that are contained into different access units.

Genomic Data Classification

The sequence reads generated by sequencing machines are classified by the disclosed invention into 5 different "Classes" according to the results of the alignment with respect to one or more reference sequences or genomes.

When aligning a DNA sequence of nucleotides with respect to a reference sequence five are the possible results:
1. A region in the reference sequence is found to match the sequence read without any error (perfect mapping). Such sequence of nucleotides will be referenced to as "perfectly matching read" or denoted as "Class P"
2. A region in the reference sequence is found to match the sequence read with a number of mismatches constituted by a number of positions in which the sequencing machine was not able to call any base (or nucleotide). Such mismatches are denoted by an "N". Such sequences will be referenced to as "N mismatching reads" or "Class N".
3. A region in the reference sequence is found to match the sequence read with a number of mismatches constituted by a number of positions in which the sequencing machine was not able to call any base (or nucleotide) OR a different base than the one reported in the reference sequence has been called. Such type of mismatch is called Single Nucleotide Variation (SNV) or Single Nucleotide Polymorphism (SNP). The sequence will be referenced to as "M mismatching reads" or "Class M".
4. A fourth class is constituted by sequencing reads presenting a mismatch type that includes the same mismatches of class M plus the presence of insertions or deletions (a.k.a. indels). Insertions are represented by a sequence of one or more nucleotides not present in the reference, but present in the read sequence. In literature when the inserted sequence is at the edges of the sequence it is referred to as "soft clipped" (i.e. the nucleotides are not matching the reference but are kept in the aligned reads contrarily to "hard clipped" nucleotides which are discarded). Keeping or discarding nucleotides is typically a user's decisions implemented as a configuration of the aligning tool. Deletion are "holes" (missing nucleotides) in the aligned read with respect to the reference. Such sequences will be referenced to as "I mismatching reads" or "Class I".
5. A fifth class includes all reads that do now find any valid mapping on the reference sequence according to the specified alignment constraints. Such sequences are said to be Unmapped and belonging to "Class U"

Unmapped reads can be assembled into a single sequence using de-novo assembly algorithms. Once the new sequence has been created unmapped reads can be further mapped with respect to it and be classified in one of the 4 classes P, N, M and I.

The data structure of said genomic data requires the storage of global parameters and metadata to be used by the decoding engine. These data are structured in a main header described in the table below.

TABLE 1

| \multicolumn{3}{c}{Main Header structure} | | |
| --- | --- | --- |
| Element | Type | Description |
| Unique ID | Byte array | Unique identifier for the encoded content |
| Version | Byte array | Major + Minor version of the encoding algorithm |
| Header Size | Integer | Size in bytes of the entire encoded content |
| Reads Length | Integer | Size of reads in case of constant reads length. A special value (e.g. 0) is reserved for variable reads length |
| Ref count | Integer | Number of reference sequences used |
| Access Units counters | Byte array (e.g. integers) | Total Number of encoded Access Units per reference sequence |
| Ref ids | Byte array | Unique identifiers for reference sequences |
| Master index table Alignment positions of first read in each block (Access Unit). I.e. smaller position of the first read on the reference genome per each block of the 4 classes 1 per pos class (4) per reference | Byte array (e.g. integers) | This is a multidimensional array supporting random access to Access Units. |

Once the classification of reads is completed with the definition of the Classes, further processing consists in defining a set of distinct syntax elements which represent the remaining information enabling the reconstruction of the DNA read sequence when represented as being mapped on a given reference sequence. A DNA segment referred to a given reference sequence can be fully expressed by:

The starting position on the reference sequence (pos).
A flag signaling if the read has to be considered as a reverse complement versus the reference (rcomp).
A distance to the mate pair in case of paired reads (pair).
The value of the read length in case of the sequencing technology produces variable length reads. In case of constant reads length the read length associated to each reads can obviously be omitted and can be stored in the main file header.
For each mismatch:
  Mismatch position (nmis for class N, snpp for class M, and indp for class I)
  Mismatch type (not present in class N, snpt in class M, indt in class I)
Flags indicating specific characteristics of the sequence read such as:
  template having multiple segments in sequencing
  each segment properly aligned according to the aligner
  unmapped segment
  next segment in the template unmapped
  signalization of first or last segment
  quality control failure
  PCR or optical duplicate
  secondary alignment
  supplementary alignment
Optional soft clipped nucleotides string when present (indc in class I)

This classification creates groups of descriptors (syntax elements) that can be used to univocally represent genome sequence reads. The table below summarizes the syntax elements needed for each class of aligned reads.

TABLE 2

Defined layers per class of data.

|       | P | N | M | I |
|-------|---|---|---|---|
| pos   | X | X | X | X |
| pair  | X | X | X | X |
| rcomp | X | X | X | X |
| flags | X | X | X | X |
| rlen  | X | X | X | X |
| nmis  |   | X |   |   |
| snpp  |   |   | X |   |
| snpt  |   |   | X |   |
| indp  |   |   |   | X |
| indt  |   |   |   | X |
| indc  |   |   |   | X |

Reads belonging to class P are characterized and can be perfectly reconstructed by only a position, a reverse complement information and an offset between mates in case they have been obtained by a sequencing technology yielding mated pairs, some flags and a read length.

The next section details how these descriptors are defined.
Position Descriptors Layer In each Access Unit, only the mapping position of the first encoded read is stored in the AU header as absolute position on the reference genome. All the other positions are expressed as a difference with respect to the previous position and are stored in a specific layer. This modeling of the information source, defined by the sequence of read positions, is in general characterized by a reduced entropy particularly for sequencing processes generating high coverage results. Once the absolute position of the first alignment has been stored, all positions of other reads are expressed as difference (distance) with respect to the first one.

For example FIG. 4 shows how after encoding the starting position of the first alignment as position "10000" on the reference sequence, the position of the second read starting at position 10180 is coded as "180". With high coverage data (>50×) most of the descriptors of the position vector will show very high occurrences of low values such as 0 and 1 and other small integers. FIG. 4 shows how the positions of three read pairs are encoded in a pos Layer.

The same source model is used for the positions of reads belonging to classes N, M, P and I. In order to enable any combination of selective access to the data, the positions of reads belonging to the four classes are encoded in separate layers as depicted in Table I.

Pairing Descriptors Layer

The pairing descriptor is stored in the pair layer. Such layer stores descriptors encoding the information needed to reconstruct the originating reads pairs, when the employed sequencing technology produces reads by pairs. Although at the date of the disclosure of the invention the vast majority of sequencing data is generated by using a technology generating paired reads, it is not the case of all technologies. This is the reason for which the presence of this layer is not necessary to reconstruct all sequencing data information if the sequencing technology of the genomic data considered does not generate paired reads information.

Definitions mate pair: read associated to another read in a read pair (e.g. Read 2 is the mate pair of Read 1 in the example of FIG. 4)
pairing distance: number of nucleotide positions on the reference sequence which separate one position in the first read (pairing anchor, e.g. last nucleotide of first read) from one position of the second read (e.g. the first nucleotide of the second read)
most probable pairing distance (MPPD): this is the most probable pairing distance expressed in number of nucleotide positions.
position pairing distance (PPD): the PPD is a way to express a pairing distance in terms of the number of reads separating one read from its respective mate present in a specific position descriptor layer.
most probable position pairing distance (MPPPD): is the most probable number of reads separating one read from its mate pair present in a specific position descriptor layer.
position pairing error (PPE): is defined as the difference between the MPPD or MPPPD and the actual position of the mate.
pairing anchor: position of first read last nucleotide in a pair used as reference to calculate the distance of the mate pair in terms of number of nucleotide positions or number of read positions.

FIG. 5 shows how the pairing distance among read pairs is calculated.

The pair descriptor layer is the vector of pairing errors calculated as number of reads to be skipped to reach the mate pair of the first read of a pair with respect to the defined decoding pairing distance.

FIG. 6 shows an example of how pairing errors are calculated, both as absolute value and as differential vector (characterized by lower entropy for high coverages).

The same descriptors are used for the pairing information of reads belonging to classes N, M, P and I. In order to enable the selective access to the different data classes, the pairing information of reads belonging to the four classes are encoded in different layer as depicted in.

Pairing Information in Case of Reads Mapped on Different References

In the process of mapping sequence reads on a reference sequence it is not uncommon to have the first read in a pair mapped on one reference (e.g. chromosome 1) and the second on a different reference (e.g. chromosome 4). In this case the pairing information described above has to be integrated by additional information related to the reference sequence used to map one of the reads. This is achieved by coding 1. A reserved value (flag) indicating that the pair is mapped on two different sequences (different values indicate if read1 or read2 are mapped on the sequence that is not currently encoded)

2. a unique reference identifier referring to the reference identifiers encoded in the main header structure as described in Table 1.

3. a third element containing the mapping information on the reference identified at point 2 and expressed as offset with respect to the last encoded position.

FIG. 7 provides an example of this scenario.

In FIG. 7, since Read 4 is not mapped on the currently encoded reference sequence, the genomic encoder signals this information by crafting additional descriptors in the pair layer. In the example shown in FIG. 7 Read 4 of pair 2 is mapped on reference no. 4 while the currently encoded reference is no. 1. This information is encoded using 3 components:

1) One special reserved value is encoded as pairing distance (in this case 0xffffff)

2) A second descriptor provides a reference ID as listed in the main header (in this case 4)

3) The third element contains the mapping information on the concerned reference (170).

Reverse Complement Descriptor Layer

Each read of the read pairs produced by sequencing technologies can be originated from either genome strands of the sequenced organic sample. However, only one of the two strands is used as reference sequence. FIG. 8 shows how in a reads pair one read (read 1) can come from one strand and the other (read 2) can come from the other.

When the strand 1 is used as reference sequence, read 2 can be encoded as reverse complement of the corresponding fragment on strand 1. This is shown in FIG. 9.

In case of coupled reads, four are the possible combinations of direct and reverse complement mate pairs. This is shown in FIG. 10. The rcomp layer codes the four possible combinations.

The same coding is used for the reverse complement information of reads belonging to classes P, N, M, I. In order to enable enhanced selective access to the data, the reverse complement information of reads belonging to the four classes are coded in different layers as depicted in Table 2.

Mismatches of Class N

Class N includes all reads which show mismatches where an 'N' is present instead of a base call. All other bases perfectly match on the reference sequence.

The positions of Ns in read 1 are encoded as
absolute position in read 1 OR
as differential position with respect to the previous N in the same read (whichever has lowest entropy).

The positions of Ns in read 2 are encoded as
absolute position in read 2+read 1 length OR
differential position with respect to the previous N (whichever has lowest entropy).

In the nmis layer, the encoding of each reads pair is terminated by a special "separator" "S" symbol. This is shown in FIG. 11.

Encoding Substitutions (Mismatches or SNPs)

A substitution is defined as the presence, in a mapped read, of a different nucleotide with respect to the one that is present in the reference sequence at the same position (see FIG. 12).

Each substitution can be encoded as
"position" (snpp layer) and "type" (snpt layer). See FIG. 13, FIG. 14, FIG. 16 and FIG. 15. OR
"position" only but using one snpp layer per mismatch type. See FIG. 17

Substitutions Positions

A substitution position is calculated as for the values of the nmis layer, i.e.: In read 1 substitutions are encoded
as absolute position in read 1 OR
as differential position with respect to the previous substitution in the same read In read 2 substitutions are encoded In read 2 substitutions are encoded:
as absolute position in read 2+read 1 length OR
as differential position with respect to the previous substitution FIG. 13 shows how substitutions positions are encoded in layer snpp. Substitutions positions can be calculated either as absolute or as differential values.

In the snpp layer, the encoding of each reads pair is terminated by a special "separator" symbol.

Substitutions Types Descriptors

For class M (and I as described in the next sections), mismatches are coded by an index (moving from right to left) from the actual symbol present in the reference to the corresponding substitution symbol present in the read {A, C, G, T, N, Z}. For example if the aligned read presents a C instead of a T which is present at the same position in the reference, the mismatch index will be denoted as "4". The decoding process reads the encoded syntax element, the nucleotide at the given position on the reference and moves from left to right to retrieve the decoded symbol. E.g. a "2" received for a position where a G is present in the reference will be decoded as "N". FIG. 14 shows all the possible substitutions and the respective encoding symbols when IUPAC ambiguity codes are not used and FIG. 15 provides an example of encoding of substitutions types in the snpt layer.

In case of presence of IUPAC ambiguity codes, the substitution indexes change as shown in FIG. 16.

In case the encoding of substation types described above presents high information entropy, an alternative method of substitution encoding consists in storing only the mismatches positions in separate layers, one per nucleotide, as depicted in FIG. 17

Coding of Insertions and Deletions

For class I, mismatches and deletions are coded by an indexes (moving from right to left) from the actual symbol present in the reference to the corresponding substitution symbol present in the read: {A, C, G, T, N, Z}. For example if the aligned read presents a C instead of a T present at the same position in the reference, the mismatch index will be "4". In case the read presents a deletion where a A is present in the reference, the coded symbol will be "5". The decoding process reads the coded syntax element, the nucleotide at the given position on the reference and moves from left to right to retrieve the decoded symbol. E.g. a "3" received for a position where a G is present in the reference will be decoded as "Z" which indicates the presence of a deletion in the sequence read.

Inserts are coded as 6, 7, 8, 9, 10 respectively for inserted A, C, G, T, N.

In case of adoption of the IUPAC ambiguity codes the substitution mechanism results to be exactly the same however the substitution vector is extended as: S={A, C, G, T, N, Z, M, R, W, S, Y, K, V, H, D, B}.

FIG. 18 and FIG. 19 show examples of how to encode substitutions, inserts and deletions in a reads pair of class I.

The following structures of file format and access units are described referring to the coding elements disclosed here above. However, the access units, the file format and the multiplexing produce the same technical advantage also with other and different algorithms of source modeling and genomic data compression.

File Format: Selective Access to Regions of Genomic Data

Master Index Table

In order to support selective access to specific regions of the aligned data, the data structure described in this document implements an indexing tool called Master Index Table (MIT). This is a multi-dimensional array containing the loci at which specific reads map on the used reference sequences. The values contained in the MIT are the mapping positions of the first read in each pos layer so that non-sequential access to each Access Unit is supported. The MIT contains one section per each class of data (P, N, M and I) and per each reference sequence. The MIT is contained in the Main Header of the encoded data. FIG. 20 shows the generic structure of the Main Header, FIG. 21 shows a generic visual representation of the MIT and FIG. 22 shows an example of MIT for the class P of encoded reads.

The values contained in the MIT depicted in FIG. 22 are used to directly access the region of interest (and the corresponding AU) in the compressed domain.

For example, with reference to FIG. 22, if it is required to access the region comprised between position 150,000 and 250,000 on reference 2, a decoding application would skip to the second reference in the MIT and would look for the two values k1 and k2 so that k1<150,000 and k2>250,000. Where k1 and k2 are 2 indexes read from the MIT. In the example of FIG. 22 this would result in positions 3 and 4 of the second vector of the MIT. These returned values will then be used by the decoding application to fetch the positions of the appropriate data from the pos layer Local Index Table as described in the next section.

Together with pointers to the layer containing the data belonging to the four classes of genomic data described above, the MIT can be used as an index of additional metadata and/or annotations added to the genomic data during its life cycle.

Local Index Table

Each data layer described above is prefixed with a data structure referred to as local header. The local header contains a unique identifier of the layer, a vector of Access Units counters per each reference sequence, a Local Index Table (LIT) and optionally some layer specific metadata. The LIT is a vector of pointers to the physical position of the data belonging to each AU in the layer payload. FIG. 23 depicts the generic layer header and payload where the LIT is used to access specific regions of the encoded data in a non-sequential way.

In the previous example, in order to access region 150,000 to 250,000 of reads aligned on the reference sequence no. 2, the decoding application retrieved positions 3 and 4 from the MIT. These values shall be used by the decoding process to access the 3rd and 4th elements of the corresponding section of the LIT. In the example shown in FIG. 24, the Total Access Units counters contained in the layer header are used to skip the LIT indexes related to AUs related to reference 1 (5 in the example). The indexes containing the physical positions of the requested AUs in the encoded stream are therefore calculated as:

position of the data blocks belonging to the requested AU=data blocks belonging to AUs of reference 1 to be skipped+position retrieved using the MIT, i.e.

First block position: 5+3=8

Last block position: 5+4=9

The blocks of data retrieved using the indexing mechanism called Local Index Table, are part of the Access Units requested.

FIG. 26 shows how the data blocks retrieved using the MIT and the LIT compose one or more Access Units.

Access Units

The genomic data classified in data classes and structured in compressed or uncompressed layers are organized into different access units.

Genomic Access Units (AU) are defined as sections of genome data (in a compressed or uncompressed form) that reconstructs nucleotide sequences and/or the relevant metadata, and/or sequence of DNA/RNA (e.g. the virtual reference) and/or annotation data generated by a genome sequencing machine and/or a genomic processing device or analysis application.

An Access Unit is a block of data that can be decoded either independently from other Access Units by using only globally available data (e.g. decoder configuration) or by using information contained in other Access Units. Access Units contain data information related to genomic data in the form of positional information (absolute and/or relative), information related to reverse complement and possibly pairing and additional data. It is possible to identify several types of access units.

Access units are differentiated by:
  type, characterizing the nature of the genomic data and data sets they carry and the way they can be accessed,
  order, providing a unique order to access units belonging to the same type.

Access units of any type can be further classified into different "categories".

Hereafter follows a non-exhaustive list of definition of different types of genomic access units:

1) Access units of type 0 do not need to refer to any information coming from other access units to be accessed or decoded and accessed (see FIG. 29). The entire information reference number carried by the data or data sets they contain can be independently read and processed by a decoding device or processing application.

2) Access units of type 1 contain data that refer to data carried by access units of type 0 (see FIG. 30). Reading or decoding and processing the data contained in access units of type 1 requires having access to one or more access units of type 0.

3) Access units of this type can contain information of mismatching or dissimilarity or uncorrespondance with respect to the information contained in the access unit of type 0.

4) Access units of type 2, 3 and 4 contain data that refer to an access unit of type 1 (see FIG. 31, FIG. 32 and FIG.

33). Reading or decoding and processing the data or data sets contained by access units of type 2, 3, and 4 requires information carried by the data or data sets contained in an access units of ty
5) pe 0 and 1. The difference among types 2, 3, and 4 access units relies in the nature of the information they contain.
6) Access units of type 5 contain metadata (e.g. quality scores) and/or annotation data associated to the data or data sets contained in the access unit of type 1. Access units of type 5 may be classified and labelled in different layers.
7) Access units of type 6 contain data or data sets classified as annotation data. Access units of type 6 may be classified and labelled in layers.
8) Access units of additional types can extend the structure and mechanisms described here. As an example, but not as a limitation, the results of genomic variant calling, structural and functional analysis can be encoded in access units of new types. The data organization in Access Units described herein does not prevent any type of data to be encapsulated in Access Units being the mechanism completely transparent with respect to the nature of encoded data.

Access units of this type can contain information of mismatching or dissimilarity or uncorrespondance with respect to the information contained in the access unit of type 0.

FIG. 28 shows how Access Units are composed by a header and one or more layers of homogeneous data. Each layer can be composed by one or more blocks. Each block contains several packets and the packets are a structured sequence of the descriptors introduced above to represent e.g. reads positions, pairing information, reverse complement information, mismatches positions and types etc.

Each Access unit can have a different number of packets in each block, but within an Access Unit all blocks have the same number of packets.

Each data packet can be identified by the combination of 3 identifiers X Y Z where:

X identifies the access unit it belongs to
Y identifies the block it belongs to (i.e. the data type it encapsulates)
Z is an identifier expressing the packet order with respect to other packets in the same block
FIG. 28 shows an example of Access Units and packets labelling.
FIG. 34 to FIG. 38 show
Access Units of several types, the common syntax to denote them is the following:
AU_T_N is an access unit of type T with identifier N which may or may not imply a notion of order according to the Access Unit Type. Identifiers are used to uniquely associate Access Units of one type with those of other types required to completely decode the carried genomic data.

Access units of any type can be classified and labelled in different "categories" according to different sequencing processes. For example, but not as a limitation, classification and labelling can take place when sequencing the same organism at different times (access units contain genomic information with a "temporal" connotation),
sequencing organic samples of different nature of the same organisms (e.g. skin, blood, hair for human samples). These are access units with "biological" connotation.
The access units of type 1, 2, 3 and 4 are built according to the result of a matching function applied on genome sequence fragments (a.k.a. reads) with respect to the reference sequence encoded in Access Units of type 0 they refer to.

For example access units (AUs) of type 1 (see FIG. 30) may contain the positions and the reverse complement flags of those reads which result in a perfect match (or maximum possible score corresponding to the selected matching function) when a matching function is applied to specific regions of the reference sequence encoded in AUs of type 0. Together with the data contained in AUs of type 0, such matching function information is sufficient to completely reconstruct all genome sequence reads represented by the data set carried by the access units of type 1.

With reference to the genomic data classification previously described in this document, the Access Units of type 1 described above would contain information related to genomic sequence reads of class P (perfect matches).

In case of variable reads length and paired reads the data contained in AUs of type 1 mentioned in the previous example, have to be integrated with the data representing the information about reads pairing and reads length in order to be able to completely reconstruct the genomic data including the reads pairs association. With respect to the data classification previously introduced in the present document, pair and rlen layers would be encoded in AU of type 1.

The matching functions applied with respect to access units of type 1 to classify the content of AU for the type 2, 3 and 4 can provide results such as:

each sequence contained in the AU of type 1 perfectly matches sequences contained in the AU of type 0 in correspondence to the specified position;
each sequence contained in the AU of type 2 perfectly matches a sequence contained in the AU of type 0 in correspondence to the specified position, except for the "N" symbols present (base not called by the sequencing device) in the sequence in the AU of type 2;
each sequence contained in the AU of type 3 includes variants in the form of substituted symbols (variants) with respect to the sequence contained in the AU of type 0 in correspondence to the specified position;
each sequence contained in the AU of type 4 includes variants in the form of substituted symbols (variants), insertions and/or deletions with respect to the sequence contained in the AU of type 0 in correspondence to the specified position.
Access units of type 0 are ordered (e.g. numbered), but they do not need to be stored and/or transmitted in an ordered manner (technical advantage: parallel processing/parallel streaming, multiplexing)

Access units of type 1, 2, 3 and 4 do not need to be ordered and do not need to be stored and/or transmitted in an ordered manner (technical advantage: parallel processing/parallel streaming).

The number of sequence reads contained in each Access Unit is a configuration parameter specified by a user by means of a user interface used when encoding the genomic data according to this invention. This configuration parameter can be sent, for example, in the header of the relevant access unit.

Technical Effects

The technical effect of structuring genomic information in access units as described here is that the genomic data:

1. can be selectively queried in order to access:
specific "categories" of data (e.g. with a specific temporal or biological connotation) without having to decompress the entire genomic data or data sets and/or the related metadata.

specific regions of the genome for all "categories", a subset of "categories", a single "category" (with or without the associated metadata) without the need to decompress other regions of the genome 2. can be incrementally updated with new data that can be available when:
   new analysis is performed on the genomic data or data sets
   new genomic data or data sets are generated by sequencing the same organisms (different biological samples, different biological sample of the same type, e.g. blood sample, but acquired at a different time, etc.)

3. can be efficiently transcoded to a new data format in case of
   new genomic data or data sets to be used as new reference (e.g. new reference genome carried by AU of type 0)
   update of the encoding format specification With respect to prior art solutions such as SAM/BAM, the aforementioned technical features address the issues of requiring data filtering to happen at the application level when the entire data has been retrieved and decompressed from the encoded format.

Hereafter follows examples of application scenario where the access unit structure becomes instrumental for a technological advantage.

Selective Access

In particular the disclosed data structure based on Access Units of different types enables to
   extract only the read information (data or data sets) of the whole sequencing of all "categories" or a subset (i.e. one or more layers) or a single "category" without having to decompress also the associated metadata information (limitation of current state of the art: SAM/BAM that cannot even support distinction between different categories or layers)
   extract all the reads aligned on specific regions of the assumed reference sequence for all categories, subsets of the categories, a single category (with or without the associated metadata) without the need to decompress also other regions of the genome (limitation of current state of the art: SAM/BAM);

FIG. 39 shows how the access to the genomic information mapped on the second segment of the reference sequence (AU 0-2) with mismatches only requires the decoding of AUs 0-2, 1-2 and 3-2 only. This is an example of selective access according to both a criteria related to a mapping region (i.e. position on the reference sequence) and a criteria related to the matching function applied to the encoded sequence reads with respect to the reference sequence (e.g. mismatches only in this example).

A further technical advantage is that the querying on the data is much more efficient in terms of data accessibility and execution speed because it can be based on accessing and decoding only selected "categories", specific regions of longer genomic sequences and only specific layers for access units of type 1, 2, 3, 4 that match the criteria of the applied queries and any combination thereof.

The organization of access units of type 1, 2, 3, 4 into layers allow for efficient extraction of nucleotides sequences
   with specific variations (e.g. mismatches, insertions, deletions) with respect to one or more reference genomes;
   that do not map to any of the considered reference genomes;
   that perfectly map on one or more reference genomes;
   that map with one or more accuracy levels Incremental Update The access units of type 5 and 6 allow for easy insertion of annotations without the need to depacketize/decode/decompress the whole file thereby adding to the efficient handling of the file which is a limitation of prior art approaches. Existing compression solutions may have to access and process a large amount of compressed data before the desired genomic data can be accessed. This will cause inefficient RAM bandwidth utilization and more power consumption also in hardware implementations. Power consumption and memory access issues may be alleviated by using the approach based on Access Units described here.

The data indexing mechanism described in the Master Index Table (see FIG. 21) together with the utilization of Access Unites enables incremental update of the encoded content as described below.

Insertion of Additional Data

New genomic information can be periodically added to existing genomic data for several reasons. For example when:
   An organism is sequenced at different moments in time;
   Several different samples of the same individual are sequenced at the same time;
   New data generated by a sequencing process (streaming).

In the above mentioned situations, structuring data using the Access Units described here and the data structure described in the file format section enables the incremental integration of the newly generated data without the need to re-encode the existing data. The incremental update process can be implemented as follows:

1. The newly generated AUs can simply be concatenated in the file with the pre-existing AUs and
2. the indexing of the newly generated data or data sets are included in the Master Index Table described in the file format section of this document. One index shall position the newly generated AU on the existing reference sequence, other indexes consist in pointers of the newly generated AUs in the physical file to enable direct and selective access to them.

This mechanism is illustrated in FIG. 40 where pre-existing data encoded in 3 AUs of type 1 and 4 AUs per each type from 2 to 4 are updated with 3 AUs per type with encoding data coming for example from a new sequence run for the same individual.

In the specific use case of streaming genomic data and data sets in compressed form, the incremental update of a pre-existing data set may be useful when analysing data as soon as they are generated by a sequencing machine and before the actual sequencing is completed. An encoding engine (compressor) can assemble several AUs in parallel by "clustering" sequence reads that map on the same region of the selected reference sequence. Once the first AU contains a number of reads above a pre-configured threshold/parameter, the AU is ready to be sent to the analysis application. Together with the newly encoded Access Unit, the encoding engine (the compressor) shall make sure that all Access Units the new AU depends on have already been sent to the receiving end or is sent together with it. For example an AU of type 3 will require the appropriate AU of type 0 and type 1 to be present at the receiving end in order to be properly decoded.

By means of the described mechanism, a receiving variant calling application would be able to start calling variants on the AU received before the sequencing process has been completed at the transmitting side. A schematic of this process is depicted in FIG. 41.

New Analysis of Results

During the genome processing life cycle several iterations of genome analysis can be applied on the same data (e.g. different variant calling using different processing algorithm). The use of AUs as defined in this document and the data structure described in the file format section of this document enable incremental update of existing compressed data with the results of new analysis.

For example, new analysis performed on existing compressed data can produce new data in these cases:
1. A new analysis can modify existing results already associated with the encoded data. This use case is depicted in FIG. 42 and it is implemented by moving entirely or partially the content of one Access Unit from one type to another. In case new AUs need to be created (due to a pre-defined maximum size per AU), the related indexes in the Master Index Table must be created and the related vector is sorted when needed.
2. New data are produced from new analysis and have to be associated to existing encoded data. In this case new AUs of type 5 can be produced and concatenated with the existing vector of AUs of the same type. This and the related update of the Master Index Table are depicted in FIG. 43.

The use cases described above and depicted in FIG. 42 and FIG. 43 are enabled by:
1. The possibility to have direct access only to data with poor mapping quality (e.g. AUs of type 4);
2. The possibility to remap reads to a new genomic region by simply creating a new Access Unit possibly belonging to a new type (e.g. reads included in a Type 4 AU can be remapped to a new region with less (type 2-3) mismatches and included in a newly created AU);
3. The possibility to create AU of type 6 containing only the newly created analysis results and/or related annotations. In this case the newly created AUs only require to contain "pointers" to the existing AUs to which they refer to.

Transcoding

Compressed genomic data can require transcoding, for example, in the following situations:

Publication of new reference sequences;

Use of a different mapping algorithm (re-mapping).

When genomic data is mapped on an existing public reference genome, the publication of a new version of said reference sequence or the desire to map the data using a different processing algorithm, today requires a process of re-mapping. When remapping compressed data using prior art file formats such as SAM or CRAM the entire compressed data has to be decompressed into its "raw" form to be mapped again with reference to the newly available reference sequence or using a different mapping algorithm. This is true even if the newly published reference is only slightly different from the previous or the different mapping algorithm used produces a mapping that is very close (or identical) to the previous mapping.

The advantage of transcoding genomic data structured using Access Units described here is that:
1. Mapping versus a new reference genome only requires re-encoding (decompressing and compressing) the data of AUs that map on the genome regions that have changes. Additionally the user may select those compressed reads that for any reason might need to be re-mapped even if they originally do not map on the changed region (this may happen if the user believes that the previous mapping is of poor quality). This use case is depicted in FIG. 44.
2. In case the newly published reference genome differs from the previous only in terms of entire regions shifted to different genomic locations ("loci"), the transcoding operation results particularly simple and efficient. In fact in order to move all the reads mapped to the "shifted" region it is sufficient to change only the value of the absolute position contained in the related (set of) AU(s) header. Each AU header contain the absolute position the first read contained in the AU is mapped to on the reference sequence, while all other reads positions are encoded differentially with respect to the first. Therefore, by simply updating the value of the absolute position of the first read, all the reads in the AU are moved accordingly. This mechanism cannot be implemented by state of the art approaches such as CRAM and BAM because genome data positions are encoded in the compressed payload, thus requiring complete decompression and re-compression of all genome data sets.
3. When a different mapping algorithm is used, it is possible to apply it only on a portion of compressed reads that was deemed mapped with poor quality. For example it can be appropriate to apply the new mapping algorithm only on reads which did not perfectly match on the reference genome. With existing formats today it is not possible (or it's only partially possible with some limitations) to extract reads according to their mapping quality (i.e. presence and number of mismatches). If new mapping results are returned by the new mapping tools the related reads can be transcoded from one AU from another of the same type (FIG. 46) or from one AU of one type to an AU of another type (FIG. 45).

Moreover, prior art compression solutions may have to access and process a large amount of compressed data before the desired genomic data can be accessed. This will cause inefficient RAM bandwidth utilization and more power consumption and in hardware implementations. Power consumption and memory access issues may be alleviated by using the approach based on Access Units described here.

A further advantage of the adoption of the genomic access units described here is the facilitation of parallel processing and suitability for hardware implementations. Current solutions such as SAM/BAM and CRAM are conceived for single-threaded software implementation.

Selective Encryption

The approach based on Access Units organized in several types an layers as described in this document enables the implementation of content protection mechanisms otherwise not possible with state of the art monolithic solutions.

A person skilled in the art knows that the majority of genomic information related to an organism's genetic profile relies in the differences (variants) with respect to a known sequence (e.g. a reference genome or a population of genomes). An individual genetic profile to be protected from unauthorized access will therefore be encoded in Access Units of type 3 and 4 as described in this document. The implementation of controlled access to the most sensible genomic information produced by a sequencing and analysis process can therefore be realized by encrypting only the payload of AUs of type3 and 4 (see FIG. 47 for an example). This will generate significant savings in terms of both processing power and bandwidth since the resources consuming encryption process shall be applied on a subset of data only.

The invention claimed is:

1. A method of compression of genomic data mapped to a reference sequence comprising partitioning a file of genomic data into data unit of different types,
wherein said partitioning is such that
data units of a first type contain genomic data, said genomic data being a portion of a reference sequence used to map the encoded data, and positional data indicating the absolute position of the first nucleotide of said portion of the reference sequence, wherein said genomic data do not refer to data units of any other type,
data units of a second type comprise genomic data classified according to the mapping on the reference genome and structured in layers of homogeneous data, the data units of the second type also contain information related to positional data indicating the position of the reads perfectly matching the part of sequence contained in the data unit of a first type, and reverse complement information with respect to the genomic information contained in the data unit of a first type, and
wherein
said positional data in the data units of the second type are stored such that the mapping position of the first read is stored as absolute position and all the other positions are expressed as a difference with respect to the previous position and stored in a specific layer, and
said positional data and reverse complement data are structured in respective different layers of homogeneous data and are compressed by applying a specific compression algorithm.

2. The method of claim 1, wherein said data units of a second type further comprise information related to genomic reads pairing and/or further information related to reads length.

3. The method of claim 1, wherein the said partitioning the genomic data into data units of different types further comprises an additional type of data unit containing information related to positions of mismatches where the sequencing machine was not able to determine any nucleotide.

4. The method of claim 1, wherein the said partitioning the genomic data into data units of different types further comprises an additional type of data unit containing information related to mismatch position and mismatch type, said mismatch relating to genomic data related to the data unit of the first type.

5. The method of claim 1, wherein the said partitioning the genomic data into data units of different types further comprises an additional type of data unit containing information related to indels and mismatches position, indels and mismatches type and information on soft clipped nucleotides and info on hard clipped nucleotides.

6. The method of claim 1, wherein the partitioning further comprises data units of another different type comprising information related metadata and/or quality scores and/or annotations data associated to the data units.

7. The method of claim 6, wherein the partitioning further comprises data units of an additional different type that comprises annotations data.

8. The method of claim 7, wherein the data of the data unit of claim 7 is organized into layers, each layer comprising information related to a different category: positional data, reverse complement, optionally paring, optionally mismatching and optionally annotations data.

9. The method of claim 1, wherein the data units contain a header and payload data.

10. The method of claim 1, wherein the data unit of second type comprises information about pairing of the reads and wherein the presence of such information is signaled in the header of the data unit.

11. The method of claim 1, wherein the number of reads comprised in a data unit of a first type is set by an input configuration parameter.

12. The method of claim 11, wherein said input configuration parameter is stored in the header of the data unit.

13. The method of claim 1, wherein the content of the data units is encrypted.

14. Apparatus comprising means suitable for carrying out the method of claim 1.

15. Storage device storing genomic data partitioned into data units according to the method of claim 1.

16. A non-transitory computer readable recording medium having recorded thereon a program comprising instruction set for executing the method of claim 1.

17. A method of compressing genomic data partitioned into data units according to the method of claim 1, wherein said data are organized as to form a file format.

18. A method of transcoding a file of genomic data partitioned into data units created according to the method of claim 1, such that when data are realigned versus a new reference genome only the payload information of the unit is modified, without having to transcode the entire file.

19. The method of claim 18, wherein the file structure is left unaltered.

20. The method of claim 19, wherein only selected data units are modified.

21. The method of claim 20, wherein the selected data units are of said first type.

22. The method of claim 21, wherein the selected data units are of any type.

* * * * *